(12) United States Patent
Wichelecki

(10) Patent No.: US 12,258,601 B2
(45) Date of Patent: Mar. 25, 2025

(54) ENZYMATIC PRODUCTION OF TAGATOSE

(71) Applicant: BONUMOSE, INC., Charlottesville, VA (US)

(72) Inventor: Daniel Joseph Wichelecki, Charlottesville, VA (US)

(73) Assignee: BONUMOSE, INC., Charlottesville, VA (US)

( * ) Notice: Subject to any disclaimer, the term of this patent is extended or adjusted under 35 U.S.C. 154(b) by 924 days.

(21) Appl. No.: 17/284,838

(22) PCT Filed: Oct. 18, 2019

(86) PCT No.: PCT/US2019/056978
§ 371 (c)(1),
(2) Date: Apr. 13, 2021

(87) PCT Pub. No.: WO2020/081959
PCT Pub. Date: Apr. 23, 2020

(65) Prior Publication Data
US 2021/0388404 A1  Dec. 16, 2021

Related U.S. Application Data

(60) Provisional application No. 62/747,877, filed on Oct. 19, 2018, provisional application No. 62/790,788, filed on Jan. 10, 2019.

(51) Int. Cl.
*C12P 19/02* (2006.01)
*C12P 19/24* (2006.01)

(52) U.S. Cl.
CPC ............. *C12P 19/02* (2013.01); *C12P 19/24* (2013.01); *C12Y 207/01144* (2013.01); *C12Y 503/01009* (2013.01); *C12Y 504/02002* (2013.01)

(58) Field of Classification Search
CPC .. C12P 19/02; C12P 19/24; C12Y 207/01144; C12Y 503/01009; C12Y 504/02002
USPC ........................................ 536/1.11
See application file for complete search history.

(56) References Cited

U.S. PATENT DOCUMENTS

| 2016/0186162 A1 | 6/2016 | Oh et al. |
| 2018/0216146 A1 | 8/2018 | Wichelecki |
| 2022/0177936 A1 | 6/2022 | Yang et al. |

FOREIGN PATENT DOCUMENTS

| EP | 0142230 A2 * | 5/1985 | ............. C12P 19/02 |
| EP | 3322803 A1 | 5/2018 | |
| KR | 101627921 B1 * | 6/2016 | ............... C12N 9/88 |
| WO | 2017/059278 A1 | 4/2017 | |
| WO | WO-2018182344 A1 * | 10/2018 | ........... C12N 9/1051 |

OTHER PUBLICATIONS

WO-2018182344-A1_PCT/US2019/056978_English Machine Translation (Year: 2018).*
UniProtKB_Accession No._A0A0P0IWV7_9EURY, Sequence Alignment, Jan. 20, 2016 (Year: 2016).*
London et al., Published Jan. 20, 2015, Biochemistry, vol. 54, pp. 528-537 (Year: 2015).*
KR-101627921-B1_English_Machine_Translation (Year: 2016).*
SEQ_9_WO_2018182344_A1, Sequence Alignment, Oct. 4, 2018 (Year: 2018).*
UniProtKB Accession No. A0A223HVJ3_THETR, Sequence Alignment, Oct. 25, 2017 (Year: 2017).*
Data base UniProt entry of Oct. 25, 2017, "Tagatose-bisphotphate aldolase", XP55941039, Acc. No. A0A223HVJ3.
Data base UniProt entry of Apr. 25, 2018, "Tagatose-bisphotphate aldolase", XP55941050, Acc. No. A0A2M8QBR9.
Data base UniProt entry of Jun. 24, 2015, "Beta-phosphoglucomutase", XP55941055, Acc. No. A0A0E3NCH4.
Data base UniProt entry of Aug. 10, 2010, "HAD-superfamily hydrolase, subfamily IA, variant 3", XP55941056, Acc. No. D6YBK5.
Data base UniProt entry of Nov. 2, 2010, "GS1-like protein {ECO:0000313 | EMBL:ADN02366.1}", XP55941058, Acc. No. E0RT70.
Data base UniProt entry of Jan. 19, 2010, "HAD-superfamily hydrolase, subfamily IA, variant 3", Acc. No. D1C7G9.
GenBank accession KPL84211.1. Oct. 2, 2015.
International Search Report and Written Opinion in International Application No. PCT/US2019/056978, dated Mar. 12, 2020.
UniProtKB Accesssion No. A0A0P0IWV7, Jan. 20, 2016.
London et al., "Covalent docking predicts substrates for haloalkanoate dehalogenase superfamily phosphates", Biochemistry, Jan. 20, 2015, vol. 54, No. 2; pp. 528-537.

\* cited by examiner

*Primary Examiner* — Yih-Horng Shiao
*Assistant Examiner* — Jaret J Crews
(74) *Attorney, Agent, or Firm* — RAPHAEL BELLUM PLLC

(57) ABSTRACT

Disclosed herein are improved processes for making tagatose including the steps of converting F6P to T6P, catalyzed by a F6PE; and converting the T6P to tagatose, catalyzed by a T6PP, using enzymes with higher activities compared to F6PEs and T6PPs previously used in a process to produce tagatose.

18 Claims, 9 Drawing Sheets

Specification includes a Sequence Listing.

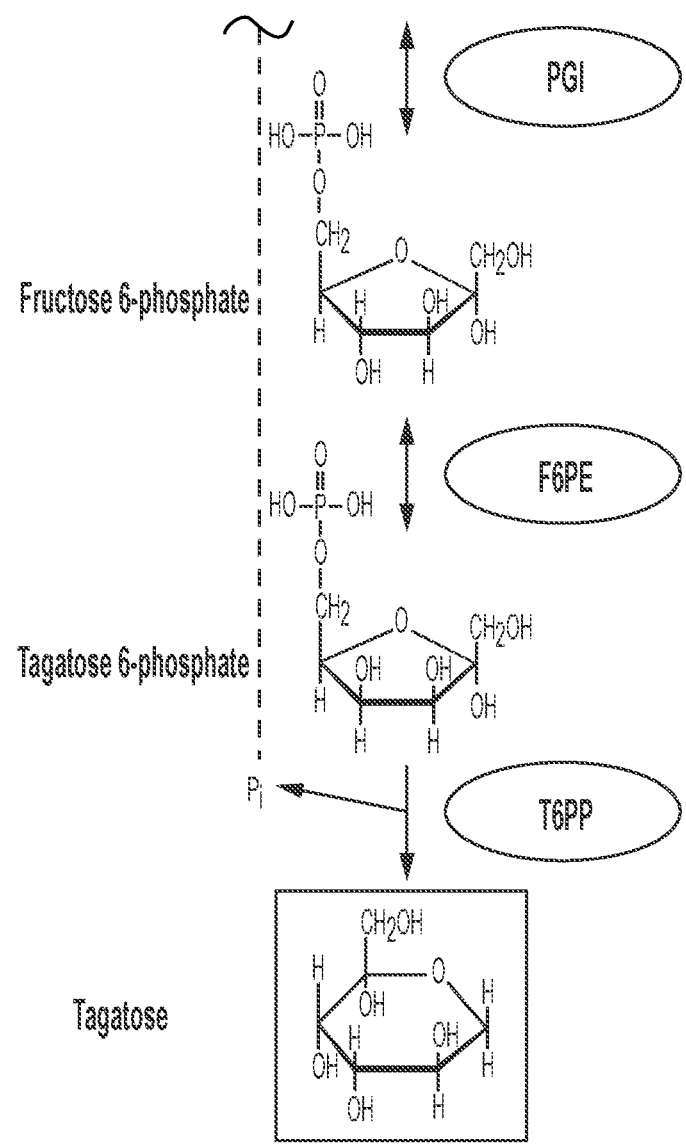
FIG. 1 - CONTINUED

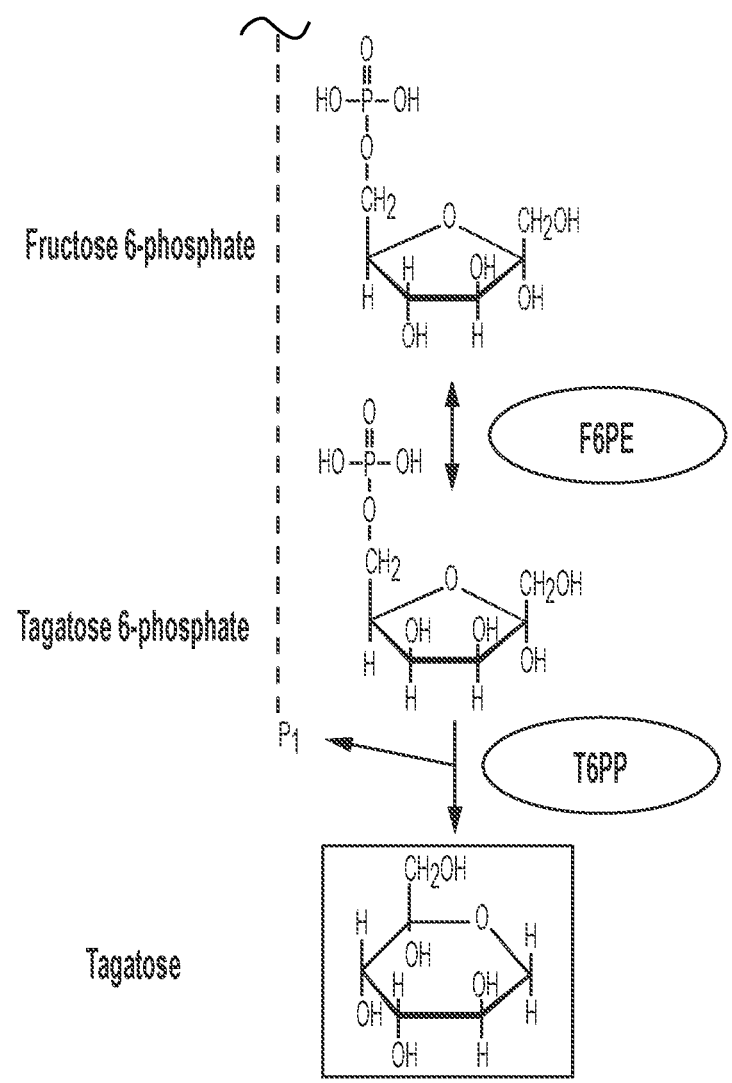
FIG. 2 - CONTINUED

SEQUENCE LISTING

<160> NUMBER OF SEQ ID NOS: 12

<210> SEQ ID NO 1
<211> LENGTH: 426
<212> TYPE: PRT
<213> ORGANISM: Thermanaerothrix daxensis

<400> SEQUENCE: 1

```
Met Val Thr Tyr Leu Asp Phe Val Val Leu Ser His Arg Phe Arg Arg
1               5                   10                  15

Pro Leu Gly Ile Thr Ser Val Cys Ser Ala His Pro Tyr Val Ile Glu
            20                  25                  30

Ala Ala Leu Arg Asn Gly Met Met Thr His Thr Pro Val Leu Ile Glu
        35                  40                  45

Ala Thr Cys Asn Gln Val Asn Gln Tyr Gly Gly Tyr Thr Gly Met Thr
    50                  55                  60

Pro Ala Asp Phe Val Arg Tyr Val Glu Asn Ile Ala Ala Arg Val Gly
65                  70                  75                  80

Ser Pro Arg Glu Asn Leu Leu Gly Gly Asp His Leu Gly Pro Leu
                85                  90                  95

Val Trp Ala His Glu Pro Ala Glu Ser Ala Met Glu Lys Ala Arg Ala
            100                 105                 110

Leu Val Lys Ala Tyr Val Glu Ala Gly Phe Arg Lys Ile His Leu Asp
        115                 120                 125

Cys Ser Met Pro Cys Ala Asp Asp Arg Asp Phe Ser Pro Lys Val Ile
    130                 135                 140

Ala Glu Arg Ala Ala Glu Leu Ala Gln Val Ala Glu Ser Thr Cys Asp
145                 150                 155                 160

Val Met Gly Leu Pro Leu Pro Asn Tyr Val Ile Gly Thr Glu Val Pro
                165                 170                 175

Pro Ala Gly Gly Ala Lys Ala Glu Ala Glu Thr Leu Arg Val Thr Arg
            180                 185                 190

Pro Glu Asp Ala Ala Glu Thr Ile Ala Leu Thr Arg Ala Ala Phe Phe
```

```
            195                 200                 205
Lys Arg Gly Leu Glu Ser Ala Trp Glu Arg Val Val Ala Leu Val Val
210                 215                 220

Gln Pro Gly Val Glu Phe Gly Asp His Gln Ile His Val Tyr Arg Arg
225                 230                 235                 240

Glu Glu Ala Gln Ala Leu Ser Arg Phe Ile Glu Ser Gln Pro Gly Leu
                245                 250                 255

Val Tyr Glu Ala His Ser Thr Asp Tyr Gln Pro Arg Asp Ala Leu Arg
                260                 265                 270

Ala Leu Val Glu Asp His Phe Ala Ile Leu Lys Val Gly Pro Ala Leu
            275                 280                 285

Thr Phe Ala Phe Arg Glu Ala Val Phe Ala Leu Ala Ser Ile Glu Asp
290                 295                 300

Trp Val Cys Asp Ser Pro Ser Arg Ile Leu Glu Val Leu Glu Thr Thr
305                 310                 315                 320

Met Leu Ala Asn Pro Val Tyr Trp Gln Lys Tyr Tyr Leu Gly Asp Glu
                325                 330                 335

Arg Ala Arg Arg Ile Ala Arg Gly Tyr Ser Phe Ser Asp Arg Ile Arg
                340                 345                 350

Tyr Tyr Trp Ser Ala Pro Ala Val Glu Gln Ala Phe Glu Arg Leu Arg
            355                 360                 365

Ala Asn Leu Asn Arg Val Ser Ile Pro Leu Val Leu Ser Gln Tyr
370                 375                 380

Leu Pro Asp Gln Tyr Arg Lys Val Arg Asp Gly Arg Leu Pro Asn Gln
385                 390                 395                 400

Phe Asp Ala Leu Ile Leu Asp Lys Ile Gln Ala Val Leu Glu Asp Tyr
                405                 410                 415

Asn Val Ala Cys Gly Val Arg Ile Gly Glu
                420                 425

<210> SEQ ID NO 2
<211> LENGTH: 434
<212> TYPE: PRT
<213> ORGANISM: Thermoanaerobacterium thermosaccharolyticum

<400> SEQUENCE: 2

Met Ala Lys Glu His Pro Leu Lys Glu Leu Val Asn Lys Gln Lys Ser
1               5                   10                  15

Gly Ile Ser Glu Gly Ile Val Ser Ile Cys Ser Ser Asn Glu Phe Val
                20                  25                  30

Ile Glu Ala Ser Met Glu Arg Ala Leu Thr Asn Gly Asp Tyr Val Leu
            35                  40                  45

Ile Glu Ser Thr Ala Asn Gln Val Asn Gln Tyr Gly Gly Tyr Ile Gly
        50                  55                  60

Met Thr Pro Ile Glu Phe Lys Lys Phe Val Phe Ser Ile Ala Lys Lys
65                  70                  75                  80

Val Asp Phe Pro Leu Asp Lys Leu Ile Leu Gly Gly Asp His Leu Gly
                85                  90                  95

Pro Leu Ile Trp Lys Asn Glu Ser Ser Asn Leu Ala Leu Ala Lys Ala
                100                 105                 110

Ser Glu Leu Ile Lys Glu Tyr Val Leu Ala Gly Tyr Thr Lys Ile His
            115                 120                 125

Ile Asp Thr Ser Met Arg Leu Lys Asp Asp Thr Asp Phe Asn Thr Glu
        130                 135                 140
```

```
Ile Ile Ala Gln Arg Ser Ala Val Leu Leu Lys Ala Ala Glu Asn Ala
145                 150                 155                 160

Tyr Met Glu Leu Asn Lys Asn Lys Asn Val Leu His Pro Val Tyr
                165                 170                 175

Val Ile Gly Ser Glu Val Pro Ile Pro Gly Gly Ser Gln Gly Ser Asp
                180                 185                 190

Glu Ser Leu Gln Ile Thr Asp Ala Lys Asp Phe Glu Asn Thr Val Glu
            195                 200                 205

Ile Phe Lys Asp Val Phe Ser Lys Tyr Gly Leu Ile Asn Glu Trp Glu
            210                 215                 220

Asn Ile Val Ala Phe Val Val Gln Pro Gly Val Glu Phe Gly Asn Asp
225                 230                 235                 240

Phe Val His Glu Tyr Lys Arg Asp Glu Ala Lys Glu Leu Thr Asp Ala
                245                 250                 255

Leu Lys Asn Tyr Lys Thr Phe Val Phe Glu Gly His Ser Thr Asp Tyr
                260                 265                 270

Gln Thr Arg Glu Ser Leu Lys Gln Met Val Glu Asp Gly Ile Ala Ile
            275                 280                 285

Leu Lys Val Gly Pro Ala Leu Thr Phe Ala Leu Arg Glu Ala Leu Ile
            290                 295                 300

Ala Leu Asn Asn Ile Glu Asn Glu Leu Leu Asn Asn Val Asp Ser Ile
305                 310                 315                 320

Lys Leu Ser Asn Phe Thr Asn Val Leu Val Ser Glu Met Ile Asn Asn
                325                 330                 335

Pro Glu His Trp Lys Asn His Tyr Phe Gly Asp Asp Ala Arg Lys Lys
            340                 345                 350

Phe Leu Cys Lys Tyr Ser Tyr Ser Asp Arg Cys Arg Tyr Tyr Leu Pro
            355                 360                 365

Thr Arg Asn Val Lys Asn Ser Leu Asn Leu Leu Ile Arg Asn Leu Glu
        370                 375                 380

Asn Val Lys Ile Pro Met Thr Leu Ile Ser Gln Phe Met Pro Leu Gln
385                 390                 395                 400

Tyr Asp Asn Ile Arg Arg Gly Leu Ile Lys Asn Glu Pro Ile Ser Leu
                405                 410                 415

Ile Lys Asn Ala Ile Met Asn Arg Leu Asn Asp Tyr Tyr Tyr Ala Ile
                420                 425                 430

Lys Pro

<210> SEQ ID NO 3
<211> LENGTH: 220
<212> TYPE: PRT
<213> ORGANISM: Methanosarcina thermophila CHTI-55

<400> SEQUENCE: 3

Met Leu Lys Ala Leu Ile Phe Asp Met Asp Gly Val Leu Val Asp Ser
1               5                   10                  15

Met Pro Phe His Ala Ala Ala Trp Lys Lys Ala Phe Phe Glu Met Gly
                20                  25                  30

Met Glu Ile Gln Asp Ser Asp Ile Phe Ala Ile Glu Gly Ser Asn Pro
            35                  40                  45

Arg Asn Gly Leu Pro Leu Leu Ile Arg Lys Ala Arg Lys Glu Pro Glu
        50                  55                  60

Ala Phe Asp Phe Glu Ala Ile Thr Ser Ile Tyr Arg Gln Glu Phe Lys
65                  70                  75                  80
```

```
Arg Val Phe Glu Pro Lys Ala Phe Glu Gly Met Lys Glu Cys Leu Glu
                85                  90                  95

Val Leu Lys Lys Arg Phe Leu Leu Ser Val Val Ser Gly Ser Asp His
            100                 105                 110

Val Ile Val His Ser Ile Ile Asn Arg Leu Phe Pro Gly Ile Phe Asp
        115                 120                 125

Ile Val Val Thr Gly Asp Asp Ile Ile Asn Ser Lys Pro His Pro Asp
    130                 135                 140

Pro Phe Leu Lys Ala Val Glu Leu Leu Asn Val Arg Arg Glu Glu Cys
145                 150                 155                 160

Val Val Ile Glu Asn Ala Ile Leu Gly Val Glu Ala Ala Lys Asn Ala
                165                 170                 175

Arg Ile Tyr Cys Ile Gly Val Pro Thr Tyr Val Glu Pro Ser His Leu
            180                 185                 190

Asp Lys Ala Asp Leu Val Val Glu Asp His Arg Gln Leu Met Gln His
        195                 200                 205

Leu Leu Ser Leu Glu Pro Ala Asn Gly Phe Arg Gln
    210                 215                 220

<210> SEQ ID NO 4
<211> LENGTH: 213
<212> TYPE: PRT
<213> ORGANISM: Thermobispora bispora strain ATCC 19993

<400> SEQUENCE: 4

Met Asp Val Val Leu Phe Asp Met Asp Gly Leu Leu Val Asp Thr Glu
1               5                   10                  15

Arg Leu Trp Phe Ala Val Glu Thr Glu Val Val Glu Arg Leu Gly Gly
            20                  25                  30

Ser Trp Gly Pro Glu His Gln Arg Gln Leu Val Gly Gly Ser Leu Lys
        35                  40                  45

Arg Ala Val Ala Tyr Met Leu Glu His Thr Gly Ala Asp Val Asp Pro
    50                  55                  60

Asp Val Val Ala Gly Trp Leu Ile Glu Gly Met Glu Arg Arg Leu Thr
65                  70                  75                  80

Glu Ser Val Asp Pro Met Pro Gly Ala Met Glu Leu Leu Thr Ala Leu
                85                  90                  95

Arg Asp Glu Gly Ile Pro Thr Gly Leu Val Thr Ser Ser Arg Arg Pro
            100                 105                 110

Leu Ala Asp Ala Val Leu Lys His Ile Gly Arg Glu His Phe Asp Val
        115                 120                 125

Val Val Thr Ala Asp Asp Val Ser His Ala Lys Pro His Pro Glu Pro
    130                 135                 140

Tyr Leu Thr Ala Leu Ala Met Leu Ser Ala Asp Pro Ala Arg Ser Val
145                 150                 155                 160

Ala Leu Glu Asp Ser Pro Asn Gly Val Ala Ser Ala Val Ala Ala Gly
                165                 170                 175

Cys Arg Val Val Ala Val Pro Ser Leu Leu Pro Ile Pro Glu Gln Pro
            180                 185                 190

Gly Val Thr Val Leu Pro Ala Leu Thr His Ala Asp Val Gly Leu Leu
        195                 200                 205

Arg Ser Leu Val Gly
    210

<210> SEQ ID NO 5
```

<211> LENGTH: 237
<212> TYPE: PRT
<213> ORGANISM: Spirochaeta thermophila ATCC 49972

<400> SEQUENCE: 5

Met Arg Lys Arg Arg Glu Cys Ala Pro Pro Gly Ile Arg Ala Ala Ile
1               5                   10                  15

Phe Asp Met Asp Gly Thr Leu Val Asn Ser Glu Asp Val Tyr Trp Asp
            20                  25                  30

Ala Asp Cys Ala Phe Leu Asp Arg Tyr Gly Ile Pro His Asp Asp Ala
        35                  40                  45

Leu Arg Glu Tyr Met Ile Gly Arg Gly Thr Lys Gly Phe Ile Glu Trp
50                  55                  60

Met Arg Thr Gln Lys Glu Ile Pro Arg Ser Asp Glu Leu Ala Arg
65                  70                  75                  80

Glu Lys Met Glu Val Phe Leu Ala His Ala Arg Gly Arg Val Gln Val
                85                  90                  95

Phe Pro Glu Met Arg Arg Leu Leu Gly Leu Glu Glu Ala Gly Met
            100                 105                 110

Pro Cys Ala Leu Ala Ser Gly Ser Pro Arg Gly Ile Ile Glu Val Leu
        115                 120                 125

Leu Glu Glu Thr Gly Leu Ala Gly Phe Phe Arg Val Val Ser Ala
130                 135                 140

Asp Glu Val Ala Arg Pro Lys Pro Ala Pro Asp Val Phe Leu Glu Ala
145                 150                 155                 160

Ala Gly Arg Leu Gly Val Glu Pro Gly Gly Cys Val Val Phe Glu Asp
                165                 170                 175

Ser Glu Pro Gly Val Arg Ala Gly Leu Asp Ala Gly Met Val Cys Val
            180                 185                 190

Ala Ile Pro Thr Leu Val Lys Asp Arg Tyr Pro Glu Val Phe Tyr Gln
        195                 200                 205

Ala Asp Val Leu Phe Glu Gly Gly Met Gly Glu Phe Ser Ala Glu Arg
    210                 215                 220

Val Trp Glu Trp Leu Gly Cys Gly Val Gly Val Gly Arg
225                 230                 235

<210> SEQ ID NO 6
<211> LENGTH: 219
<212> TYPE: PRT
<213> ORGANISM: Sphaerobacter thermophilus 20745

<400> SEQUENCE: 6

Met Ser Gln Gly Val Arg Gly Val Val Phe Asp Leu Asp Gly Leu Leu
1               5                   10                  15

Val Glu Ser Glu Glu Tyr Trp Glu Gln Ala Arg Arg Gly Phe Val Ser
            20                  25                  30

Arg Tyr Gly Gly Thr Trp Gly Asp Asp Ala Gln Gln Ala Val Met Gly
        35                  40                  45

Ala Asn Thr Arg Gln Trp Ser Arg Tyr Ile Arg Glu Ala Phe Asp Ile
50                  55                  60

Pro Leu Thr Glu Glu Ile Ala Ala Ala Val Ile Ala Arg Met Gln
65                  70                  75                  80

Glu Leu Tyr His Asp His Leu Pro Leu Leu Pro Gly Ala Ile Pro Ala
                85                  90                  95

Val Arg Ala Leu Ala Asp Arg Tyr Pro Leu Ala Val Ala Ser Ser Ser
            100                 105                 110

```
Pro Pro Val Leu Ile Arg Phe Val Leu Ala Glu Met Gly Val Ala Glu
        115                 120                 125

Cys Phe Gln Ser Val Thr Ser Ser Asp Glu Val Ala His Gly Lys Pro
    130                 135                 140

Ala Pro Asp Val Tyr His Leu Ala Cys Glu Arg Leu Gly Val Ala Pro
145                 150                 155                 160

Glu Gln Ala Val Ala Phe Glu Asp Ser Thr Ala Gly Ile Ala Ala Ala
                165                 170                 175

Leu Ala Ala Gly Leu Arg Val Ile Ala Val Pro Asn Arg Ser Tyr Pro
                180                 185                 190

Pro Asp Pro Asp Val Leu Arg Arg Ala Asp Leu Thr Leu Pro Ser Leu
        195                 200                 205

Glu Glu Phe Asp Pro Ala Val Leu Glu Gln Trp
        210                 215

<210> SEQ ID NO 7
<211> LENGTH: 424
<212> TYPE: PRT
<213> ORGANISM: Candidatus Thermofonsia Clade 3 bacterium

<400> SEQUENCE: 7

Met Thr Tyr Leu Asp Tyr Leu Thr Ala Ser His His Ser Gly Lys Pro
1               5                   10                  15

Ile Gly Leu Ser Ser Ile Cys Ser Ala His Pro Trp Val Leu Arg Thr
            20                  25                  30

Ala Leu Gln Gly Glu Arg Pro Val Leu Ile Glu Ser Thr Cys Asn Gln
        35                  40                  45

Val Asn Gln Phe Gly Gly Tyr Ser Gly Met Lys Pro Ala Asp Phe Val
    50                  55                  60

Arg Phe Val His Ser Leu Ala Ala Glu Asn Gly Phe Pro Thr Glu Lys
65                  70                  75                  80

Ile Leu Leu Gly Gly Asp His Leu Gly Pro Ser Pro Trp Gln Asn Glu
                85                  90                  95

Pro Ala Glu Gln Ala Met Ala Lys Ala Ile Glu Met Val Arg Ala Tyr
            100                 105                 110

Val Gln Ala Gly Tyr Thr Lys Ile His Leu Asp Cys Ser Met Pro Leu
        115                 120                 125

Gly Gly Glu Arg Gln Leu Pro Val Glu Val Ile Ala Gln Arg Thr Val
    130                 135                 140

Gln Leu Ala Glu Ala Ala Glu Gln Ala Ala His Glu Ser Arg Leu Thr
145                 150                 155                 160

Ser His Thr Leu Arg Tyr Val Ile Gly Ser Glu Val Pro Pro Pro Gly
                165                 170                 175

Gly Ala Ile Gly Pro His Glu Gly Leu Arg Val Thr Pro Val Glu Glu
            180                 185                 190

Ala Arg Gln Thr Leu Glu Val Met Gln Ala Ala Phe His Gln Ala Gly
        195                 200                 205

Leu Glu Ala Ala Trp Glu Arg Val Arg Ala Leu Val Val Gln Pro Gly
    210                 215                 220

Val Glu Phe Gly Asp Asp Phe Val His Asp Tyr Asp Pro Ala Ala Ala
225                 230                 235                 240

Ala Gly Leu Ala Arg Phe Ile Glu Thr Val Pro Asn Leu Val Tyr Glu
                245                 250                 255

Ala His Ser Thr Asp Tyr Gln Thr Pro Glu Ser Leu Ala Ala Leu Val
```

```
                        260             265             270
Arg Asp His Phe Ala Ile Leu Lys Val Gly Pro Ala Leu Thr Phe Ala
            275             280             285

Leu Arg Glu Ala Val Phe Ala Leu Ala Met Ile Glu Asn Glu Leu Phe
        290             295             300

Pro Ala Glu Glu Arg Ser His Leu Val Glu Arg Leu Glu Ala Ala Met
305             310             315             320

Leu Arg Gln Pro Gly His Trp Gln Arg His Tyr His Gly Glu Arg
            325             330             335

Gln Gln Ala Leu Ala Arg Lys Tyr Ser Phe Ser Asp Arg Ile Arg Tyr
            340             345             350

Tyr Trp Gly Asp Pro Asp Val Gln Ala Ala Phe Arg Gln Leu Leu Ala
            355             360             365

Asn Leu Glu Arg Val Ala Pro Leu Pro Leu Thr Leu Leu Ser Gln Tyr
            370             375             380

Leu Pro Glu Met Phe Gly Glu Ile Arg Arg Gly Leu Leu Leu Asn His
385             390             395             400

Pro Ala Ala Phe Leu Glu Arg Lys Ile Gln Ala Val Leu Asp Thr Tyr
            405             410             415

Arg Ala Ala Cys Gly Glu Glu Asp
            420
```

<210> SEQ ID NO 8
<211> LENGTH: 822
<212> TYPE: PRT
<213> ORGANISM: Thermotoga maritima

<400> SEQUENCE: 8

```
Met Leu Glu Lys Leu Pro Glu Asn Leu Lys Glu Leu Glu Ser Leu Ala
1               5                   10                  15

Tyr Asn Leu Trp Trp Ser Trp Ser Arg Pro Ala Gln Arg Leu Trp Arg
            20                  25                  30

Met Ile Asp Ser Glu Lys Trp Glu Glu His Arg Asn Pro Val Lys Ile
        35                  40                  45

Leu Arg Glu Val Ser Lys Glu Arg Leu Glu Glu Leu Ser Lys Asp Glu
    50                  55                  60

Asp Phe Ile Ala Leu Tyr Glu Leu Thr Leu Glu Arg Phe Thr Asp Tyr
65                  70                  75                  80

Met Glu Arg Glu Asp Thr Trp Phe Asn Val Asn Tyr Pro Glu Trp Asp
                85                  90                  95

Glu Lys Ile Val Tyr Met Cys Met Glu Tyr Gly Leu Thr Lys Ala Leu
            100                 105                 110

Pro Ile Tyr Ser Gly Gly Leu Gly Ile Leu Ala Gly Asp His Leu Lys
        115                 120                 125

Ser Ala Ser Asp Leu Gly Leu Pro Leu Ile Ala Val Gly Leu Leu Tyr
    130                 135                 140

Lys His Gly Tyr Phe Thr Gln Gln Ile Asp Ser Asp Gly Arg Gln Ile
145                 150                 155                 160

Glu Ile Phe Pro Glu Tyr Asp Ile Glu Glu Leu Pro Met Lys Pro Leu
                165                 170                 175

Arg Asp Glu Asp Gly Asn Gln Val Ile Val Glu Val Pro Ile Asp Asn
            180                 185                 190

Asp Thr Val Lys Ala Arg Val Phe Glu Val Gln Val Gly Arg Val Lys
        195                 200                 205
```

-continued

```
Leu Tyr Leu Leu Asp Thr Asp Phe Glu Glu Asn Glu Asp Arg Phe Arg
    210             215                 220
Lys Ile Cys Asp Tyr Leu Tyr Asn Pro Glu Pro Asp Val Arg Val Ser
225             230                 235                 240
Gln Glu Ile Leu Leu Gly Ile Gly Met Lys Leu Leu Lys Thr Leu
                245                 250                 255
Lys Ile Lys Pro Gly Val Ile His Leu Asn Glu Gly His Pro Ala Phe
            260                 265                 270
Ser Ser Leu Glu Arg Ile Lys Ser Tyr Met Glu Glu Gly Tyr Ser Phe
        275                 280                 285
Thr Glu Ala Leu Glu Ile Val Arg Gln Thr Thr Val Phe Thr Thr His
    290                 295                 300
Thr Pro Val Pro Ala Gly His Asp Arg Phe Pro Phe Asp Phe Val Glu
305                 310                 315                 320
Lys Lys Leu Thr Lys Phe Phe Glu Gly Phe Glu Ser Lys Glu Leu Leu
                325                 330                 335
Met Asn Leu Gly Lys Asp Glu Asp Gly Asn Phe Asn Met Thr Tyr Leu
            340                 345                 350
Ala Leu Arg Thr Ser Ser Phe Ile Asn Gly Val Ser Lys Leu His Ala
        355                 360                 365
Asp Val Ser Arg Arg Met Phe Lys Asn Val Trp Lys Gly Val Pro Val
    370                 375                 380
Glu Glu Ile Pro Ile Glu Gly Ile Thr Asn Gly Val His Met Gly Thr
385                 390                 395                 400
Trp Ile Asn Arg Glu Met Arg Lys Leu Phe Asp Arg Tyr Leu Gly Arg
                405                 410                 415
Val Trp Arg Glu His Thr Asp Leu Glu Gly Ile Trp Tyr Gly Val Asp
            420                 425                 430
Arg Ile Pro Asp Glu Glu Leu Trp Glu Ala His Leu Asn Ala Lys Lys
        435                 440                 445
Arg Phe Ile Asp Tyr Ile Arg Glu Ser Ile Lys Arg Arg Asn Glu Arg
    450                 455                 460
Leu Gly Ile Asn Glu Pro Leu Pro Glu Ile Ser Glu Asn Val Leu Ile
465                 470                 475                 480
Ile Gly Phe Ala Arg Arg Phe Ala Thr Tyr Lys Arg Ala Val Leu Leu
                485                 490                 495
Phe Ser Asp Leu Glu Arg Leu Lys Arg Ile Val Asn Asn Ser Glu Arg
            500                 505                 510
Pro Val Tyr Ile Val Tyr Ala Gly Lys Ala His Pro Arg Asp Glu Gly
        515                 520                 525
Gly Lys Glu Phe Leu Arg Arg Ile Tyr Glu Val Ser Gln Met Pro Asp
    530                 535                 540
Phe Lys Asn Lys Ile Ile Val Leu Glu Asn Tyr Asp Ile Gly Met Ala
545                 550                 555                 560
Arg Leu Met Val Ser Gly Val Asp Val Trp Leu Asn Asn Pro Arg Arg
                565                 570                 575
Pro Met Glu Ala Ser Gly Thr Ser Gly Met Lys Ala Ala Ala Asn Gly
            580                 585                 590
Val Leu Asn Ala Ser Val Tyr Asp Gly Trp Trp Val Glu Gly Tyr Asn
        595                 600                 605
Gly Arg Asn Gly Trp Val Ile Gly Asp Glu Ser Val Leu Pro Glu Thr
    610                 615                 620
Glu Ala Asp Asp Pro Lys Asp Ala Glu Ala Leu Tyr Glu Leu Leu Glu
```

```
                625                 630                 635                 640
        Asn Glu Ile Ile Pro Thr Tyr Tyr Glu Asn Arg Glu Lys Trp Ile Phe
                        645                 650                 655

Met Met Lys Glu Ser Ile Lys Ser Val Ala Pro Lys Phe Ser Thr Thr
                        660                 665                 670

Arg Met Leu Lys Glu Tyr Thr Glu Lys Phe Tyr Ile Lys Gly Leu Val
                        675                 680                 685

Asn Arg Glu Trp Leu Glu Arg Arg Glu Asn Val Glu Lys Ile Gly Ala
                        690                 695                 700

Trp Lys Glu Arg Ile Leu Lys Asn Trp Glu Asn Val Ser Ile Glu Arg
        705                 710                 715                 720

Ile Val Leu Glu Asp Ser Lys Ser Val Glu Val Thr Val Lys Leu Gly
                        725                 730                 735

Asp Leu Thr Pro Asn Asp Val Ile Val Glu Leu Val Ala Gly Arg Gly
                        740                 745                 750

Glu Gly Met Glu Asp Leu Glu Val Trp Lys Val Ile His Ile Arg Arg
                        755                 760                 765

Tyr Arg Lys Glu Asn Asp Leu Phe Val Tyr Thr Tyr Thr Asn Gly Val
                        770                 775                 780

Leu Gly His Leu Gly Ser Pro Gly Trp Phe Tyr Ala Val Arg Val Ile
        785                 790                 795                 800

Pro Tyr His Pro Arg Leu Pro Ile Lys Phe Leu Pro Glu Val Pro Val
                        805                 810                 815

Val Trp Lys Lys Val Leu
                        820

<210> SEQ ID NO 9
<211> LENGTH: 456
<212> TYPE: PRT
<213> ORGANISM: Thermococcus kodakaraensis

<400> SEQUENCE: 9

Met Gly Lys Leu Phe Gly Thr Phe Gly Val Arg Gly Ile Ala Asn Glu
1               5                   10                  15

Glu Ile Thr Pro Glu Phe Ala Leu Lys Ile Gly Met Ala Phe Gly Thr
                20                  25                  30

Leu Leu Lys Arg Glu Gly Arg Glu Arg Pro Leu Val Val Val Gly Arg
            35                  40                  45

Asp Thr Arg Val Ser Gly Glu Met Leu Lys Asp Ala Leu Ile Ser Gly
        50                  55                  60

Leu Leu Ser Thr Gly Cys Asp Val Ile Asp Val Gly Ile Ala Pro Thr
65                  70                  75                  80

Pro Ala Ile Gln Trp Ala Thr Asn His Phe Asn Ala Asp Gly Gly Ala
                85                  90                  95

Val Ile Thr Ala Ser His Asn Pro Pro Glu Tyr Asn Gly Ile Lys Leu
                100                 105                 110

Leu Glu Pro Asn Gly Met Gly Leu Lys Lys Glu Arg Glu Ala Ile Val
            115                 120                 125

Glu Glu Leu Phe Phe Ser Glu Asp Phe His Arg Ala Lys Trp Asn Glu
        130                 135                 140

Ile Gly Glu Leu Arg Lys Glu Asp Ile Ile Lys Pro Tyr Ile Glu Ala
145                 150                 155                 160

Ile Lys Asn Arg Val Asp Val Glu Ala Ile Lys Lys Arg Arg Pro Phe
                165                 170                 175
```

Val Val Val Asp Thr Ser Asn Gly Ala Gly Ser Leu Thr Leu Pro Tyr
            180                 185                 190

Leu Leu Arg Glu Leu Gly Cys Lys Val Val Ser Val Asn Ala His Pro
        195                 200                 205

Asp Gly His Phe Pro Ala Arg Asn Pro Glu Pro Asn Glu Glu Asn Leu
    210                 215                 220

Lys Gly Phe Met Glu Ile Val Lys Ala Leu Gly Ala Asp Phe Gly Val
225                 230                 235                 240

Ala Gln Asp Gly Asp Ala Asp Arg Ala Val Phe Ile Asp Glu Asn Gly
                245                 250                 255

Arg Phe Ile Gln Gly Asp Lys Thr Phe Ala Leu Val Ala Asp Ala Val
            260                 265                 270

Leu Arg Glu Asn Gly Gly Gly Leu Leu Val Thr Thr Ile Ala Thr Ser
        275                 280                 285

Asn Leu Leu Asp Asp Ile Ala Lys Arg Asn Gly Ala Lys Val Met Arg
    290                 295                 300

Thr Lys Val Gly Asp Leu Ile Val Ala Arg Ala Leu Leu Glu Asn Asn
305                 310                 315                 320

Gly Thr Ile Gly Gly Glu Glu Asn Gly Gly Val Ile Phe Pro Asp Phe
                325                 330                 335

Val Leu Gly Arg Asp Gly Ala Met Thr Thr Ala Lys Ile Val Glu Ile
            340                 345                 350

Phe Ala Lys Ser Gly Lys Lys Phe Ser Glu Leu Ile Asp Glu Leu Pro
        355                 360                 365

Lys Tyr Tyr Gln Phe Lys Thr Lys Arg His Val Glu Gly Asp Arg Lys
    370                 375                 380

Ala Ile Val Ala Lys Val Ala Glu Leu Ala Glu Lys Lys Gly Tyr Lys
385                 390                 395                 400

Ile Asp Thr Thr Asp Gly Thr Lys Ile Ile Phe Asp Gly Trp Val
                405                 410                 415

Leu Val Arg Ala Ser Gly Thr Glu Pro Ile Ile Arg Ile Phe Ser Glu
            420                 425                 430

Ala Lys Ser Glu Glu Lys Ala Arg Glu Tyr Leu Glu Leu Gly Ile Lys
        435                 440                 445

Leu Leu Glu Glu Ala Leu Lys Gly
    450                 455

<210> SEQ ID NO 10
<211> LENGTH: 408
<212> TYPE: PRT
<213> ORGANISM: Dictyoglomus thermophilum

<400> SEQUENCE: 10

Met Trp Leu Ser Lys Asp Tyr Leu Arg Lys Lys Gly Val Tyr Ser Ile
1               5                   10                  15

Cys Ser Ser Asn Pro Tyr Val Ile Glu Ala Ser Val Glu Phe Ala Lys
            20                  25                  30

Glu Lys Asn Asp Tyr Ile Leu Ile Glu Ala Thr Pro His Gln Ile Asn
        35                  40                  45

Gln Phe Gly Gly Tyr Ser Gly Met Thr Pro Asp Phe Lys Asn Phe
    50                  55                  60

Val Met Gly Ile Ile Lys Glu Lys Gly Ile Glu Glu Asp Arg Val Ile
65                  70                  75                  80

Leu Gly Gly Asp His Leu Gly Pro Leu Pro Trp Gln Asp Glu Pro Ser
                85                  90                  95

Ser Ser Ala Met Lys Lys Ala Lys Asp Leu Ile Arg Ala Phe Val Glu
            100                 105                 110

Ser Gly Tyr Lys Lys Ile His Leu Asp Cys Ser Met Ser Leu Ser Asp
            115                 120                 125

Asp Pro Val Val Leu Ser Pro Glu Lys Ile Ala Glu Arg Glu Arg Glu
130                 135                 140

Leu Leu Glu Val Ala Glu Thr Ala Arg Lys Tyr Asn Phe Gln Pro
145                 150                 155                 160

Val Tyr Val Val Gly Thr Asp Val Pro Val Ala Gly Gly Glu Glu
            165                 170                 175

Glu Gly Ile Thr Ser Val Glu Asp Phe Arg Val Ala Ile Ser Ser Leu
            180                 185                 190

Lys Lys Tyr Phe Glu Asp Val Pro Arg Ile Trp Asp Arg Ile Ile Gly
            195                 200                 205

Phe Val Ile Met Leu Gly Ile Gly Phe Asn Tyr Glu Lys Val Phe Glu
            210                 215                 220

Tyr Asp Arg Ile Lys Val Arg Lys Ile Leu Glu Glu Val Lys Lys Glu
225                 230                 235                 240

Asn Leu Phe Val Glu Gly His Ser Thr Asp Tyr Gln Thr Lys Arg Ala
            245                 250                 255

Leu Arg Asp Met Val Glu Asp Gly Val Arg Ile Leu Lys Val Gly Pro
            260                 265                 270

Ala Leu Thr Ala Ser Phe Arg Arg Gly Val Phe Leu Leu Ser Ser Ile
            275                 280                 285

Glu Asp Glu Leu Ile Ser Asp Lys Arg Ser Asn Ile Lys Lys Val
            290                 295                 300

Val Leu Glu Thr Met Leu Lys Asp Asp Lys Tyr Trp Arg Lys Tyr Tyr
305                 310                 315                 320

Lys Asp Ser Glu Arg Leu Glu Leu Asp Ile Trp Tyr Asn Leu Leu Asp
            325                 330                 335

Arg Ile Arg Tyr Tyr Trp Glu Tyr Lys Glu Ile Lys Ile Ala Leu Asn
            340                 345                 350

Arg Leu Phe Glu Asn Phe Ser Glu Gly Val Asp Ile Arg Tyr Ile Tyr
            355                 360                 365

Gln Tyr Phe Tyr Asp Ser Tyr Phe Lys Val Arg Glu Gly Lys Ile Arg
            370                 375                 380

Asn Asp Pro Arg Glu Leu Ile Lys Asn Glu Ile Lys Lys Val Leu Glu
385                 390                 395                 400

Asp Tyr His Tyr Ala Val Asn Leu
            405

<210> SEQ ID NO 11
<211> LENGTH: 223
<212> TYPE: PRT
<213> ORGANISM: Archaeoglobus fugidis

<400> SEQUENCE: 11

Met Phe Lys Pro Lys Ala Ile Ala Val Asp Ile Asp Gly Thr Leu Thr
1               5                   10                  15

Asp Arg Lys Arg Ala Leu Asn Cys Arg Ala Val Glu Ala Leu Arg Lys
            20                  25                  30

Val Lys Ile Pro Val Ile Leu Ala Thr Gly Asn Ile Ser Cys Phe Ala
            35                  40                  45

Arg Ala Ala Ala Lys Leu Ile Gly Val Ser Asp Val Val Ile Cys Glu

```
            50                  55                  60
Asn Gly Gly Val Val Arg Phe Glu Tyr Asp Gly Glu Asp Ile Val Leu
 65                  70                  75                  80

Gly Asp Lys Glu Lys Cys Val Glu Ala Val Arg Val Leu Glu Lys His
                 85                  90                  95

Tyr Glu Val Glu Leu Leu Asp Phe Glu Tyr Arg Lys Ser Glu Val Cys
                100                 105                 110

Met Arg Arg Ser Phe Asp Ile Asn Glu Ala Arg Lys Leu Ile Glu Gly
                115                 120                 125

Met Gly Val Lys Leu Val Asp Ser Gly Phe Ala Tyr His Ile Met Asp
                130                 135                 140

Ala Asp Val Ser Lys Gly Lys Ala Leu Lys Phe Val Ala Glu Arg Leu
145                 150                 155                 160

Gly Ile Ser Ser Ala Glu Phe Ala Val Ile Gly Asp Ser Glu Asn Asp
                165                 170                 175

Ile Asp Met Phe Arg Val Ala Gly Phe Gly Ile Ala Val Ala Asn Ala
                180                 185                 190

Asp Glu Arg Leu Lys Glu Tyr Ala Asp Leu Val Thr Pro Ser Pro Asp
                195                 200                 205

Gly Glu Gly Val Val Glu Ala Leu Gln Phe Leu Gly Leu Leu Arg
                210                 215                 220

<210> SEQ ID NO 12
<211> LENGTH: 659
<212> TYPE: PRT
<213> ORGANISM: Thermococcus litoralis

<400> SEQUENCE: 12

Met Glu Arg Ile Asn Phe Ile Phe Gly Ile His Asn His Gln Pro Leu
  1               5                  10                  15

Gly Asn Phe Gly Trp Val Phe Glu Glu Ala Tyr Asn Arg Ser Tyr Arg
                 20                  25                  30

Pro Phe Met Glu Ile Leu Glu Glu Phe Pro Glu Met Lys Val Asn Val
                 35                  40                  45

His Phe Ser Gly Pro Leu Leu Glu Trp Ile Glu Glu Asn Lys Pro Asp
                 50                  55                  60

Tyr Leu Asp Leu Leu Arg Ser Leu Ile Lys Arg Gly Gln Leu Glu Ile
 65                  70                  75                  80

Val Val Ala Gly Phe Tyr Glu Pro Val Leu Ala Ala Ile Pro Lys Glu
                 85                  90                  95

Asp Arg Leu Val Gln Ile Glu Met Leu Lys Asp Tyr Ala Arg Lys Leu
                100                 105                 110

Gly Tyr Asp Ala Lys Gly Val Trp Leu Thr Glu Arg Val Trp Gln Pro
                115                 120                 125

Glu Leu Val Lys Ser Leu Arg Glu Ala Gly Ile Glu Tyr Val Val Val
                130                 135                 140

Asp Asp Tyr His Phe Met Ser Ala Gly Leu Ser Lys Glu Glu Leu Phe
145                 150                 155                 160

Trp Pro Tyr Tyr Thr Glu Asp Gly Gly Glu Val Ile Thr Val Phe Pro
                165                 170                 175

Ile Asp Glu Lys Leu Arg Tyr Leu Ile Pro Phe Arg Pro Val Lys Lys
                180                 185                 190

Thr Ile Glu Tyr Leu Glu Ser Leu Thr Ser Asp Asp Pro Ser Lys Val
                195                 200                 205
```

-continued

```
Ala Val Phe His Asp Asp Gly Glu Lys Phe Gly Val Trp Pro Gly Thr
210                 215                 220
Tyr Glu Trp Val Tyr Glu Lys Gly Trp Leu Arg Glu Phe Phe Asp Ala
225                 230                 235                 240
Ile Thr Ser Asn Glu Lys Ile Asn Leu Met Thr Tyr Ser Glu Tyr Leu
            245                 250                 255
Ser Lys Phe Thr Pro Arg Gly Leu Val Tyr Leu Pro Ile Ala Ser Tyr
        260                 265                 270
Phe Glu Met Ser Glu Trp Ser Leu Pro Ala Lys Gln Ala Lys Leu Phe
    275                 280                 285
Val Glu Phe Val Glu Gln Leu Lys Glu Gly Lys Phe Glu Lys Tyr
290                 295                 300
Arg Val Phe Val Arg Gly Gly Ile Trp Lys Asn Phe Phe Lys Tyr
305                 310                 315                 320
Pro Glu Ser Asn Phe Met His Lys Arg Met Leu Met Val Ser Lys Ala
                325                 330                 335
Val Arg Asp Asn Pro Glu Ala Arg Lys Tyr Ile Leu Lys Ala Gln Cys
            340                 345                 350
Asn Asp Ala Tyr Trp His Gly Val Phe Gly Gly Ile Tyr Leu Pro His
        355                 360                 365
Leu Arg Arg Thr Val Trp Glu Asn Ile Ile Lys Ala Gln Arg Tyr Leu
370                 375                 380
Lys Pro Glu Asn Lys Ile Leu Asp Val Asp Phe Asp Gly Arg Ala Glu
385                 390                 395                 400
Ile Met Val Glu Asn Asp Gly Phe Ile Ala Thr Ile Lys Pro His Tyr
                405                 410                 415
Gly Gly Ser Ile Phe Glu Leu Ser Ser Lys Arg Lys Ala Val Asn Tyr
            420                 425                 430
Asn Asp Val Leu Pro Arg Arg Trp Glu His Tyr His Glu Val Pro Glu
        435                 440                 445
Ala Thr Lys Pro Glu Lys Glu Ser Glu Glu Gly Ile Ala Ser Ile His
    450                 455                 460
Glu Leu Gly Lys Gln Ile Pro Glu Glu Ile Arg Arg Glu Leu Ala Tyr
465                 470                 475                 480
Asp Trp Gln Leu Arg Ala Ile Leu Gln Asp His Phe Ile Lys Pro Glu
                485                 490                 495
Glu Thr Leu Asp Asn Tyr Arg Leu Val Lys Tyr His Glu Leu Gly Asp
            500                 505                 510
Phe Val Asn Gln Pro Tyr Glu Tyr Glu Met Ile Glu Asn Gly Val Lys
        515                 520                 525
Leu Trp Arg Glu Gly Gly Val Tyr Ala Glu Glu Lys Ile Pro Ala Arg
    530                 535                 540
Val Glu Lys Lys Ile Glu Leu Thr Glu Asp Gly Phe Ile Ala Lys Tyr
545                 550                 555                 560
Arg Val Leu Leu Glu Lys Pro Tyr Lys Ala Leu Phe Gly Val Glu Ile
                565                 570                 575
Asn Leu Ala Val His Ser Val Met Glu Lys Pro Glu Glu Phe Glu Ala
            580                 585                 590
Lys Glu Phe Glu Val Asn Asp Pro Tyr Gly Ile Gly Lys Val Arg Ile
        595                 600                 605
Glu Leu Asp Lys Ala Ala Lys Val Trp Lys Phe Pro Ile Lys Thr Leu
    610                 615                 620
Ser Gln Ser Glu Ala Gly Trp Asp Phe Ile Gln Gln Gly Val Ser Tyr
```

-continued

```
            625                 630                 635                 640
Thr Met Leu Phe Pro Ile Glu Lys Glu Leu Glu Phe Thr Val Arg Phe
                    645                 650                 655
Arg Glu Leu
```

ENZYMATIC PRODUCTION OF TAGATOSE

CROSS REFERENCE TO RELATED APPLICATIONS

This application claims priority to U.S. Application No. 62/747,877, filed on Oct. 19, 2018, and to U.S. Application No. 62/790,788, filed on Jan. 10, 2019, each herein incorporated by reference.

FIELD OF THE INVENTION

The invention relates to the field of biotechnology pertaining to D-tagatose production. More specifically, the invention provides improved D-tagatose preparation methods capable of enzymatically converting saccharides (e.g., polysaccharides, oligosaccharides, disaccharides, sucrose, D-glucose, and D-fructose) into D-tagatose.

BACKGROUND

D-tagatose (tagatose hereafter) is a low-calorie, natural sweetener that has 92% the sweetness of sucrose, but only 38% of the calories. Due to its high selling prices, its use as a sweetener has been limited. Tagatose boasts a myriad of health benefits: it is non-cariogenic; it is low-calorie; it has a very low glycemic index of 3; it attenuates the glycemic index of glucose by 20%; it can lower average blood glucose levels; it helps prevent cardiovascular disease, strokes, and other vascular diseases by promoting high-density lipoprotein (HDL) cholesterol; and it is a verified prebiotic and antioxidant. Lu et al., Tagatose, a New Antidiabetic and Obesity Control Drug, *Diabetes Obes. Metab.* 10(2): 109-34 (2008). As such, tagatose clearly has a variety of applications in consumable products and in a variety of industries, such as the pharmaceutical, biotechnological, academic, food, beverage, dietary supplement, and grocery industries.

Tagatose is produced predominantly through the hydrolysis of lactose by lactase to form D-glucose and D-galactose (see WO 2011/150556, CN 103025894, U.S. Pat. Nos. 5,002,612, 6,057,135, and 8,802,843). The D-galactose is then isomerized to D-tagatose either chemically by calcium hydroxide under alkaline conditions or enzymatically by L-arabinose isomerase under pH neutral conditions. The final product is isolated by a combination of filtration and ion exchange chromatography. This method suffers because of the costly separation of D-glucose and D-galactose, and low product yields. Several methods via microbial cell fermentation are being developed, but none have been proven to be a practical alternative due to their dependence on costly feedstock (e.g., galactitol and D-psicose), low product yields, and costly separation. Other processes for preparing tagatose have also been reported. See e.g., Lee et al., Scientific Reports|7: 1934|DOI:10.1038/s41598-017-02211-3, pp. 1-8; U.S. Patent Publication No. 2018/0023073; International Patent Application Publication Nos. WO 2014/196811, WO 2018/004310, WO 2018/021894, WO 2018/182344, WO 2018/182345, WO 2018/182354, WO 2018/182355, and WO 2016/064146.

International Patent Application Publication No. WO 2017/059278 recently described the enzymatic synthesis of tagatose, in a process that involves a steps of converting fructose 6-phosphate (F6P) to tagatose 6-phosphate (T6P), catalyzed by an epimerase, fructose 6-phosphate epimerase, and a step of converting the T6P to tagatose, catalyzed by a phosphatase, tagatose 6-phosphate phosphatase. However, despite improvements in enzymatic tagatose production, there is still a desire and need for providing further improved processes of producing tagatose that can, e.g., provide a higher yield with lower amounts of enzymes. There is a strong industrial and commercial interest in decreasing the cost of tagatose production, and this decrease involves the use of a reduced amount of enzymes and use of combinations of enzymes that are more effective than previously used enzymes.

SUMMARY OF THE INVENTION

The invention provides improved tagatose preparation methods capable of enzymatically converting saccharides (e.g., polysaccharides, oligosaccharides, disaccharides, sucrose, D-glucose, and D-fructose) into tagatose. In one aspect, an improved process of the invention for the production of tagatose from a saccharide includes a step of converting fructose-6-phosphate (F6P) to tagatose 6-phopsphate (T6P) using a fructose 6-phosphate epimerase (F6PE) wherein the F6PE comprises an amino acid sequence having at least 90% sequence identity to SEQ ID NO: 1, SEQ ID NO: 2, or SEQ ID NO: 7. In another aspect, an improved process according to the invention for the production of tagatose from a saccharide includes a step of converting T6P to tagatose using tagatose-6-phoshpate phosphatase (T6PP), wherein the T6PP comprises an amino acid sequence having at least 90% sequence identity to SEQ ID NO: 3, SEQ ID NO: 4, SEQ ID NO: 5, or SEQ ID NO: 6. In some embodiments of the invention, the improved process includes a step of converting fructose-6-phosphate (F6P) to tagatose 6-phopsphate (T6P) using a fructose 6-phosphate epimerase (F6PE) wherein the F6PE comprises an amino acid sequence having at least 90% sequence identity to SEQ ID NO: 1, SEQ ID NO: 2, or SEQ ID NO: 7, and a step of converting T6P to tagatose using a tagatose-6-phoshpate phosphatase (T6PP), wherein the T6PP comprises an amino acid sequence having at least 90% sequence identity to SEQ ID NO: 3, SEQ ID NO: 4, SEQ ID NO: 5, or SEQ ID NO: 6.

In some improved processes of the invention, the process for preparing tagatose also involves the step of converting glucose 6-phosphate (G6P) to the F6P, where the step is catalyzed by phosphoglucose isomerase (PGI). Some processes according to the invention further include the step of converting glucose 1-phosphate (G1P) to the G6P catalyzed by phosphoglucomutase (PGM). Some process of the invention further include the steps of converting a saccharide to G1P, catalyzed by at least one enzyme.

The saccharides used in any of the processes can be selected from the group consisting of a starch or its derivative, cellulose or its derivative, and sucrose. The starch or its derivative can be amylose, amylopectin, soluble starch, amylodextrin, maltodextrin, maltose, maltotriose, or glucose. In some improved processes of the invention, the process for preparing tagatose involves converting starch to a starch derivative by enzymatic hydrolysis or by acid hydrolysis of starch. In other processes, a starch derivative is prepared by enzymatic hydrolysis of starch catalyzed by isoamylase, pullulanase, alpha-amylase, or a combination of two or more of these enzymes. Some processes of the invention can additionally involve adding 4-glucan transferase (4GT).

Other processes of the invention for preparing tagatose further include a step of converting fructose to F6P, catalyzed by at least one enzyme. Other processes of the invention further include a step of converting sucrose to the fructose, catalyzed by at least one enzyme. G6P to be used in some processes for preparing tagatose can also be generated by converting glucose to the G6P, catalyzed by at least one enzyme. Glucose can in turn be produced by converting sucrose to glucose, catalyzed by at least one enzyme.

Process of the invention are conducted under reaction conditions including at a temperature ranging from about 37C to about 85° C., at a pH ranging from about 5.0 to about 9.0, and/or for about 1 hour to about 48 hours, or as continuous reactions. In some embodiments, the steps of a process for preparing tagatose are conducted under those reaction conditions in one bioreactor. In other embodiments, the steps are conducted under those reaction conditions in a plurality of bioreactors arranged in series.

In some processes of the invention, the steps for preparing tagatose are conducted ATP-free, NAD(H)-free, at a phosphate concentration from about 0.1 mM to about 150 mM, the phosphate is recycled, and/or the step of converting T6P to tagatose involves an energetically favorable chemical reaction.

DETAILED DESCRIPTION

Figure 1:
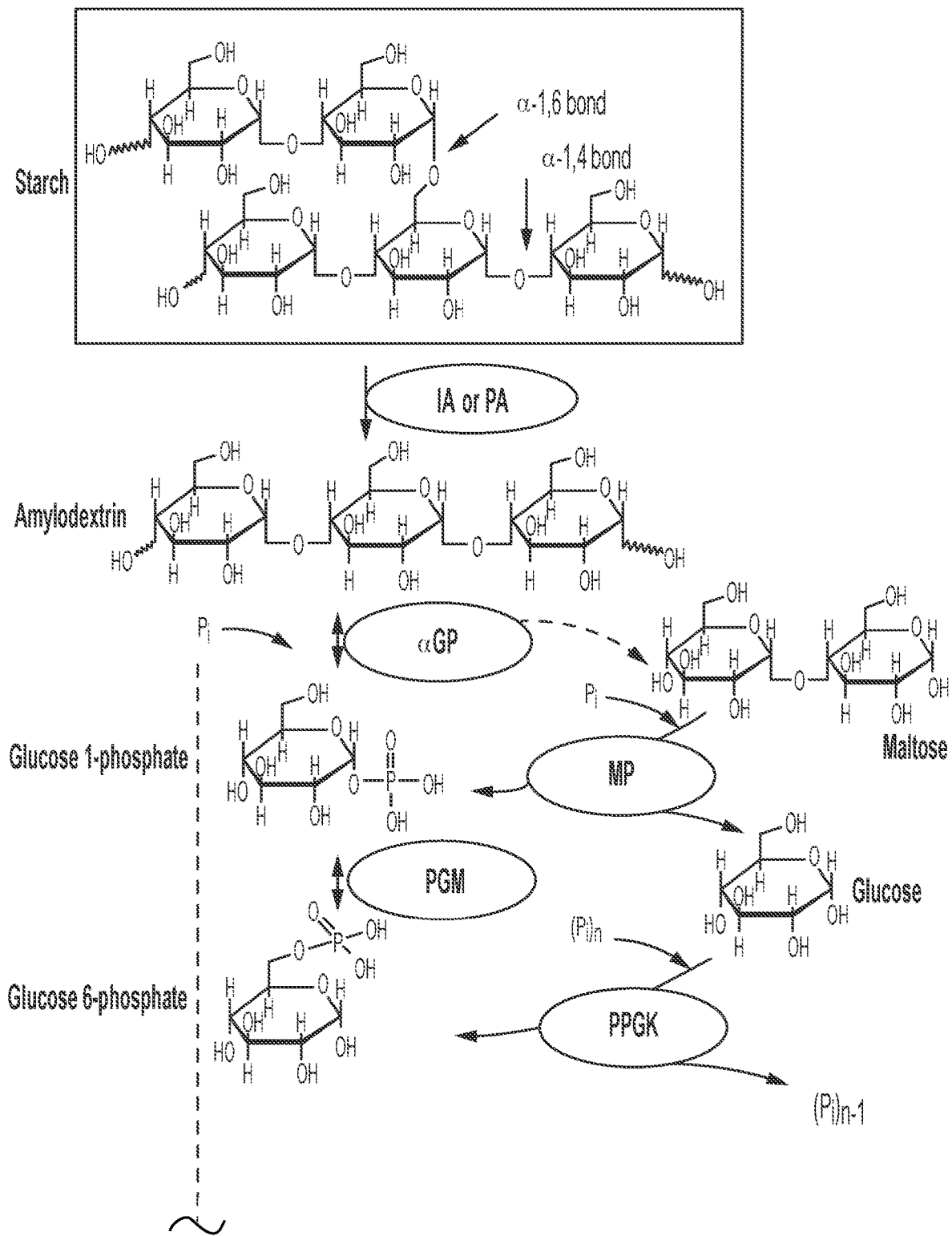
FIG. 1 is a schematic diagram illustrating an enzymatic pathway converting starch or its derived products to tagatose. The following abbreviations are used: αGP, alpha-glucan phosphorylase or starch phosphorylase; PGM, phosphoglucomutase; PGI, phosphoglucoisomerase; F6PE, fructose 6-phosphate epimerase; T6PP, tagatose 6-phosphate phosphatase; IA, isoamylase; PA, pullulanase; MP, maltose phosphorylase; PPGK, polyphosphate glucokinase.

The invention generally relates to improved enzymatic processes for the conversion of saccharides to tagatose. For example, the invention relates to improved processes for the conversion of saccharides such as starch, cellulose, sucrose, glucose, and fructose and their derived products to tagatose using cell-free enzyme cocktails. In contrast to cell-based manufacturing methods, the invention involves a cell-free preparation of tagatose, has relatively high reaction rates due to the elimination of the cell membrane, which often slows down the transport of substrate/product into and out of the cell. The processes of the invention also result in a final product free of nutrient-rich fermentation media/cellular metabolites.

In one aspect, the invention relates to improved processes for making tagatose including the steps of converting F6P to T6P, catalyzed by a F6PE; and converting the T6P to tagatose, catalyzed by a T6PP, using enzymes with improved activities compared to F6PEs and/or T6PPs previously used in a process to produce tagatose. See e.g., International Patent Application Publication WO2017/059278, disclosing F6PEs and T6PPs: F6PE from *Anaerolinea thermophila* UNI-1 (Uniprot ID E8N0N6); F6PE from *Caldicellulosiruptor kronotskyensis* (Uniprot ID E4SEH3); F6PE from *Caldilinea aerophila* (Uniprot ID 101507); F6PE from *Caldithrix abyssi* (Uniprot ID H1XRG1); and F6PE from *Dictyoglomus thermophilum* (Uniprot ID B5YBD7); T6PP from *Archaeoglobus fulgidus* (Uniprot ID 029805); T6PP from *Archaeoglobus profundus* (Uniprot ID D2RHV2_ARCPA); and T6PP from *Archaeoglobus veneficus* (Uniprot ID F2KMK2_ARCVS). Using enzymes with higher activities allows for using lower amounts of enzymes, thereby reducing the cost of the overall process.

In the improved processes of the invention, F6PEs have a higher activity compared to that of the previously disclosed Thermophilic F6PE from *Dictyoglomus thermophilum* (Uniprot ID B5YBD7). See International Patent Application Publication WO2017/059278. Preferably, F6PEs used in the processes of the invention have an enzymatic activity improved by at least 10%, at least 30%, at least 80%, at least 100%, at least 150%, at least 180% or at least 200%, relative to the activity of Thermophilic F6PE from *Dictyoglomus thermophilum* (Uniprot ID B5YBD7). For instance, as shown in Example 1, Thermophilic F6PE from *Thermanaerothrix daxensis* (Uniprot A0A0P6XN50) has enzymatic activity improved by approximately 150% relative to Thermophilic F6PE from *Dictyoglomus thermophilum* (Uniprot ID: B5YBD7), Thermophilic F6PE from Candidatus Thermofonsia Clade 3 (Uniprot ID A0A2M8QBR9) has enzymatic activity improved by approximately 120% relative to Thermophilic F6PE from *Dictyoglomus thermophilum* (Uniprot ID: B5YBD7), and Thermophilic F6PE from *Thermoanaerobacterium thermosaccharolyticum* (Uniprot A0A223HVJ3) has enzymatic activity improved by approximately 178% relative to Thermophilic F6PE from *Dictyoglomus thermophilum* (Uniprot ID B5YBD7). The examples below provide protocols to those skilled in the art for determining activity of F6PEs, which involve incubating the enzyme with its substrate, and then measuring the amounts of reactants and products via HPLC. Measurements of relative activities any two enzymes are performed under identical reaction conditions such as buffer, pH, temperature, etc.

F6PEs used in processes of the invention are specific for F6P and T6P; the epimerization catalyzed by F6PE is a reversible reaction. Specific means having a higher activity for F6P/T6P over other phosphorylated monosaccharides present in the reaction. For instance, F6PE has a higher epimerization activity on F6P/T6P than on, for example, G6P.

Examples of F6PEs for use in the improved process of the invention include but are not limited to the following proteins: Thermophilic F6PE from *Thermanaerothrix daxensis* (Uniprot ID A0A0P6XN50) with the amino acid sequence as listed in SEQ ID NO: 1; Thermophilic F6PE from *Thermoanaerobacterium thermosaccharolyticum* (Uniprot ID A0A223HVJ3) with the amino acid sequence as listed in SEQ ID NO: 2; Thermophilic F6PE from Candidatus Thermofonsia Clade 3 (Uniprot ID A0A2M8QB119), with the amino acid sequence as listed in SEQ ID NO: 7; and F6PEs having at least 90%, at least 95%, at least 97%, at least 99%, or 100% amino acid sequence identity to SEQ ID NO: 1, SEQ ID NO: 2, or SEQ ID NO: 7. An improved process for the production of tagatose from a saccharide according to the invention includes the step of converting fructose-6-phosphate (F6P) to tagatose 6-phopsphate (T6P) using a F6PE, where the F6PE comprises an amino acid sequence having at least 90%, amino acid sequence identity to SEQ ID NO: 1, SEQ ID NO: 2, or SEQ ID NO: 7.

F6PEs used in processes of the invention are epimerases which can convert F6P to T6P. F6PEs utilize a divalent metal cofactor, such as magnesium, manganese, cobalt, or zinc, preferably magnesium F6PEs for use in processes of the invention comprises an amino acid sequence having at least 90% at least 95%, at least 97%, at least 99%, or 100%, amino acid sequence identity to SEQ ID NO: 1, SEQ ID NO: 2, or SEQ ID NO: 7, and preferably contain an aldolase-type TIM barrel. See Wichelecki et al., (2015) J. Biol. Chem., v290, pp. 28963-76.

In the improved processes of the invention, T6PPs have a higher activity compared to that of the previously disclosed T6PP from *Archaeoglobus fulgidus* (Uniprot ID O29805). See International Patent Application Publication WO2017/059278. Preferably, T6PPs used in the processes of the invention have an enzymatic activity improved by at least 10%, at least 30%, at least 80%, at least 100%, at least 150%, at least 300%, at least 500%, at least 600%, at least 900%, at least 1200%, at least 1500%, at least 1800%, or at least 2100% relative to the activity of T6PP from *Archaeoglobus fulgidus* (Uniprot ID O29805). For instance, as shown in Example 2, T6PP from *Methanosarcina thermophila* CHTI-55 (Uniprot ID A0A0E3NCH4) has enzymatic activity improved by approximately 614% relative to T6PP from *Archaeoglobus fulgidus* (Uniprot ID O29805), T6PP from *Thermobispora bispora* strain ATCC 19993 (Uniprot D6YBK5) has enzymatic activity improved by approximately 1328% relative to T6PP from *Archaeoglobus fulgidus* (Uniprot ID O29805), T6PP from *Spirochaeta thermophila* ATCC 49972 (Uniprot ID E0RT70) has enzymatic activity improved by approximately 2075% relative to T6PP from *Archaeoglobus fulgidus* (Uniprot ID O29805), and T6PP from *Sphaerobacter thermophilus* DSM 20745 (Uniprot ID D1C7G9) has enzymatic activity improved by approximately 814% relative to T6PP from *Archaeoglobus fulgidus* (Uniprot ID O29805). The examples below provide protocols to those skilled in the art for determining activity of T6PPs, which involve incubating the enzyme with its substrate, and then measuring the amounts of reactants and products via HPLC. Measurements of relative activities any two enzymes are performed under identical reaction conditions such as buffer, pH, temperature, etc.

T6PPs used in processes of the invention are specific for T6P. For T6PP, specific means having a higher dephosphorylation activity on T6P over other phosphorylated monosaccharides in the process. For instance, T6PP has a higher dephosphorylation activity on T6P than on, for example G1P, G6P, and F6P.

Examples of T6PPs for use in the processes of the invention include but are not limited to the following proteins: a T6PP from *Methanosarcina thermophila* CHTI-55 (Uniprot ID A0A0E3NCH4) with the amino acid sequence as listed in SEQ ID NO: 3; a T6PP from *Thermobispora bispora* strain ATCC 19993 (Uniprot ID D6YBK5) with the amino acid sequence as listed in SEQ ID NO: 4; a T6PP from *Spirochaeta thermophila* strain ATCC 49972 (Uniprot ID E0RT70) with the amino acid sequence as listed in SEQ ID NO: 5; a T6PP from *Sphaerobacter thermophilus* strain DSM 20745 (Uniprot ID D1C7G9) with the amino acid sequence as listed in SEQ ID NO: 6; and T6PPs having at least 90%, at least 95%, at least 97%, at least 99%, or 100% amino acid sequence identity to SEQ ID NO: 3, SEQ ID NO: 4, SEQ ID NO: 5, or SEQ ID NO: 6. A process according to the invention for the production of tagatose from a saccharide includes converting fructose-6-phosphate (F6P) to tagatose 6-phopsphate (T6P) using a fructose 6-phosphate epimerase (F6PE) and converting the T6P produced to tagatose using a tagatose-6-phoshpate phosphatase (T6PP), where the T6PP comprises an amino acid sequence having at least 90% sequence identity to SEQ ID NO: 3, SEQ ID NO: 4, SEQ ID NO: 5, or SEQ ID NO: 6.

In processes of the invention, T6PPs are phosphatases which convert T6P to tagatose. T6PPs utilize a divalent metal cofactor, such as zinc, manganese, cobalt, or magnesium, preferably magnesium. In processes of the invention, T6PPs have at least 90%, at least 95%, at least 97%, at least 99%, or 100% amino acid sequence identity to SEQ ID NO: 3, SEQ ID NO: 4, SEQ ID NO: 5, or SEQ ID NO: 6; and preferably contain a Rossmanoid fold domain for catalysis and additionally, a Cl capping domain for substrate specificity; a DxD signature in the $1^{st}$ β-strand of the Rossmanoid fold for coordinating magnesium, where the second Asp is a general acid/base catalyst; a Thr or Ser at the end of the $2^{nd}$ β-strand of the Rossmanoid fold that helps stability of reaction intermediates; a Lys at the N-terminus of the α-helix C-terminal to the $3^{rd}$ β-strand of the Rossmanoid fold that helps stability of reaction intermediates; and a E(D/N) signature at the end of the $4^{th}$ β-strand of the Rossmanoid fold for coordinating divalent metal cations, such as magnesium. See e.g., Burroughs et al., Evolutionary Genomics of the HAD Superfamily: Understanding the Structural Adaptations and Catalytic Diversity in a Superfamily of Phosphoesterases and Allied Enzymes. J. Mol. Biol. 2006; 361; 1003-1034.

A preferred enzymatic process according to the invention includes a step of converting fructose-6-phosphate (F6P) to tagatose 6-phopsphate (T6P) using a fructose 6-phosphate epimerase (F6PE) where the F6PE comprises an amino acid sequence having at least 90% sequence identity to SEQ ID NO: 1, SEQ ID NO: 2, or SEQ ID NO: 7, and a step of converting T6P to tagatose using a tagatose-6-phoshpate phosphatase (T6PP), where the T6PP comprises an amino acid sequence having at least 90% sequence identity to SEQ ID NO: 3, SEQ ID NO: 4, SEQ ID NO: 5, or SEQ ID NO: 6. More preferably, the F6PE comprises an amino acid sequence having at least 90% sequence identity to SEQ ID NO: 2, and the T6PP comprises an amino acid sequence having at least 90% sequence identity to SEQ ID NO: 5. Most preferably, the F6PE has the amino acid sequence as listed in SEQ ID NO: 2, and the T6PP has the amino acid sequence as listed in SEQ ID NO: 5.

A process for preparing tagatose from a saccharide according to the invention also includes the step of enzymatically converting glucose 6-phosphate (G6P) to the F6P, where the step is catalyzed by phosphoglucose isomerase (PGI). Exemplary PG's which may be used include those disclosed in International Patent Application Publication WO2017/059278: PGI from *Clostridium thermocellum* (Uniprot ID A3DBX9) and PGI from *Thermus thermophilus* (Uniprot ID Q5SLL6).

A process for preparing tagatose according to the invention additionally includes the step of converting glucose 1-phosphate (G1P) to the G6P, where the step is catalyzed by phosphoglucomutase (PGM). An example of a PGM is PGM from *Thermococcus kodakaraensis* (Uniprot ID Q68BJ6), disclosed in International Patent Application Publication WO2017/059278.

Figure 2:
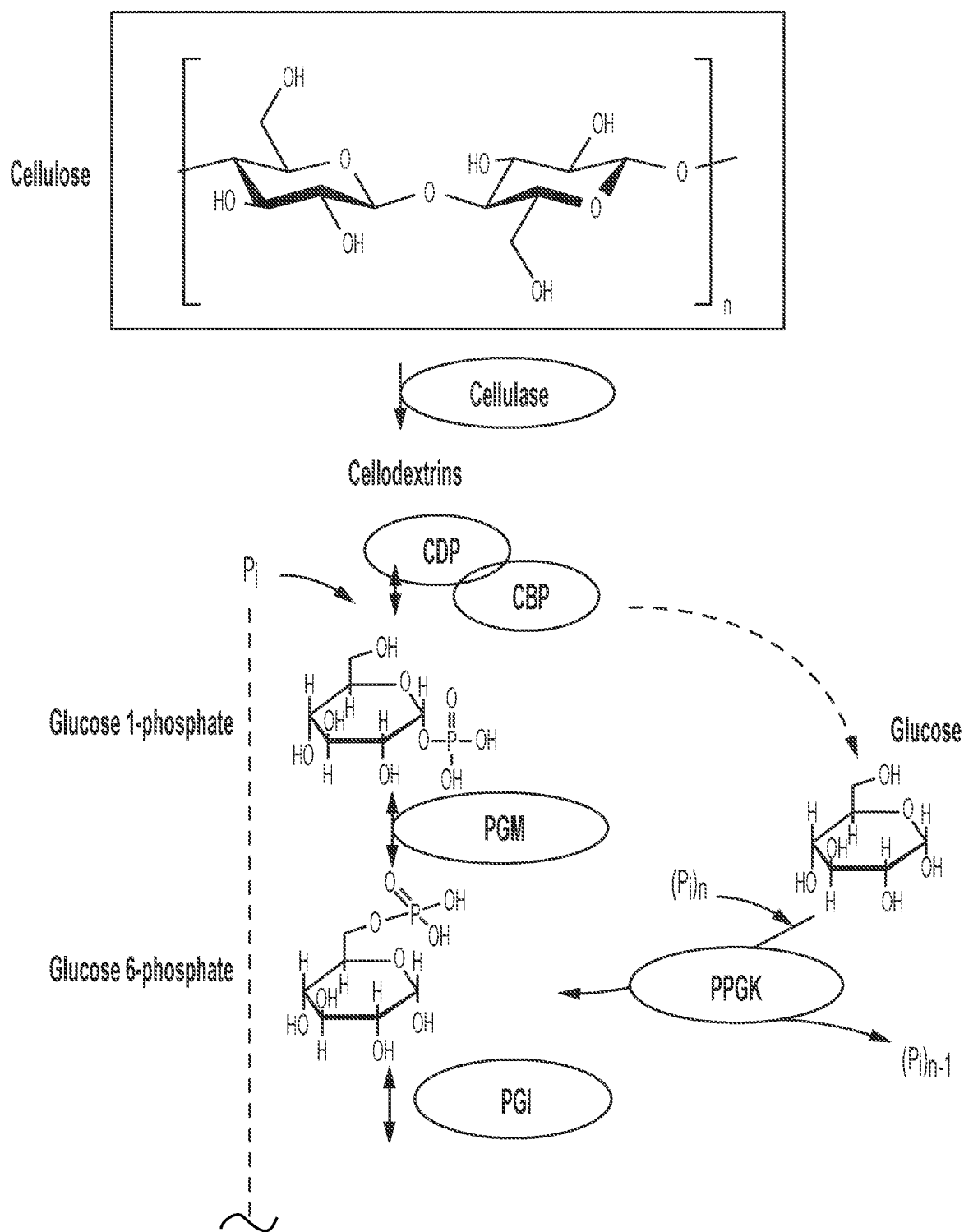
FIG. 2 shows an enzymatic pathway converting cellulose or its derived products to tagatose. CDP, cellodextrin phosphorylase; CBP, cellobiose phosphorylase; PPGK, polyphosphate glucokinase; PGM, phosphoglucomutase; PGI, phosphoglucoisomerase; F6PE, fructose 6-phosphate epimerase; T6PP, tagatose 6-phosphate phosphatase.
Figure 3:
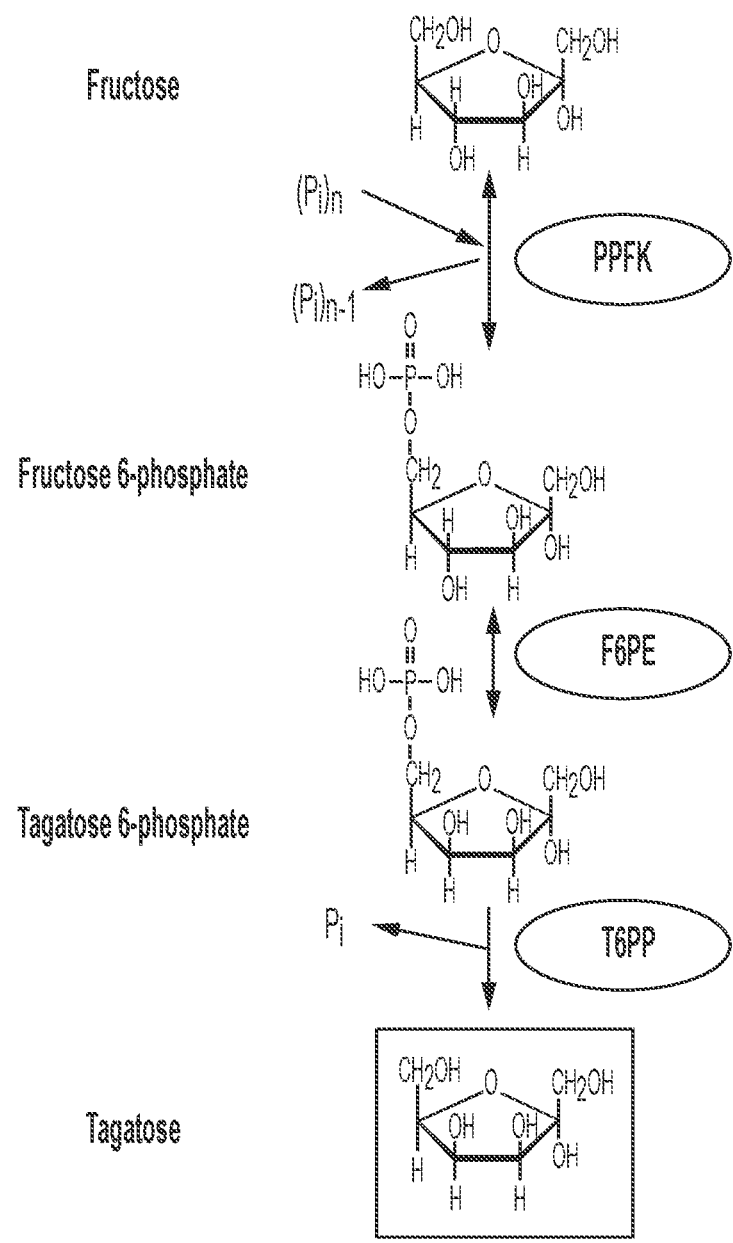
FIG. 3 is a schematic diagram illustrating an enzymatic pathway converting fructose to tagatose. PPFK, polyphosphate fructokinase; F6PE, fructose 6-phosphate epimerase; T6PP, tagatose 6-phosphate phosphatase.
Figure 4:
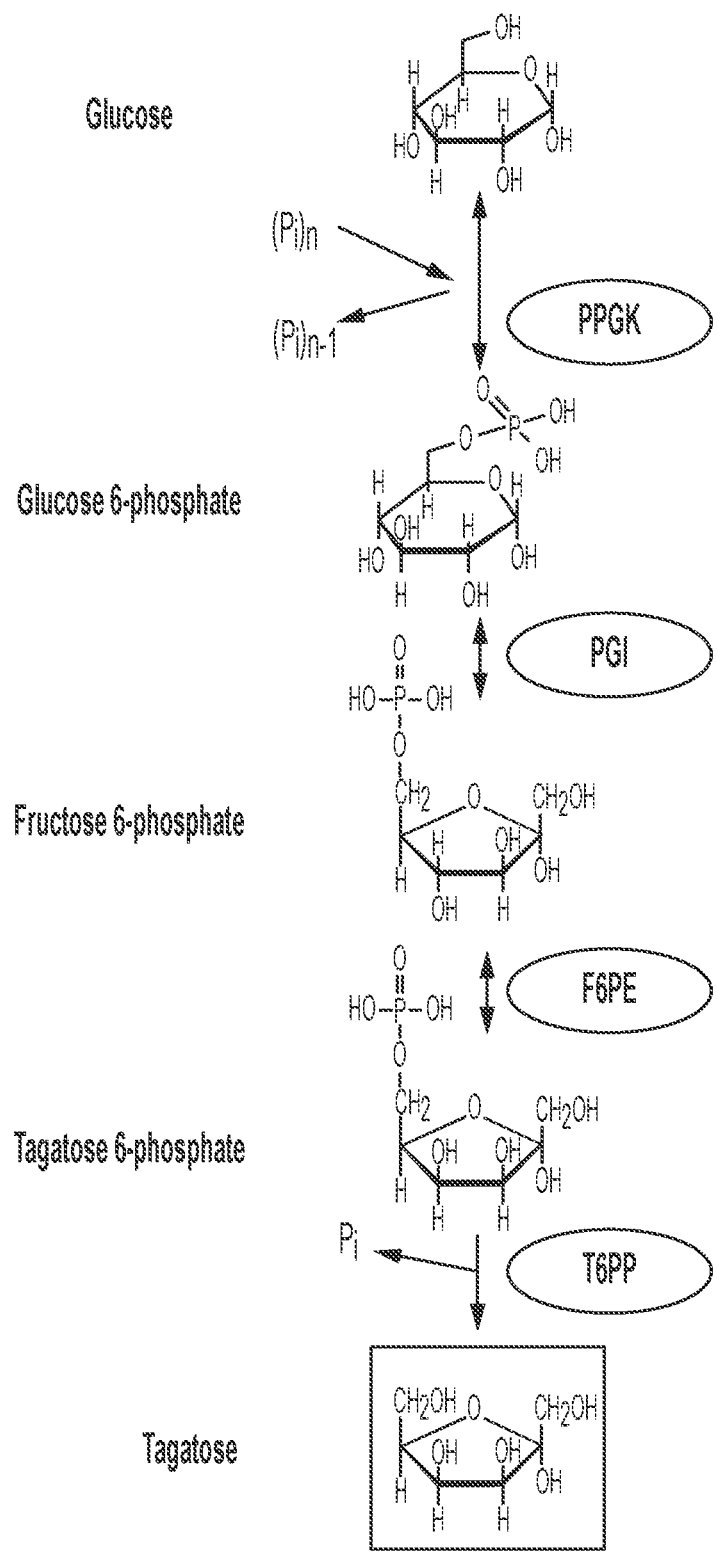
FIG. 4 is a schematic diagram illustrating an enzymatic pathway converting glucose to tagatose. PPGK, polyphosphate glucokinase; PGI, phosphoglucoisomerase; F6PE, fructose 6-phosphate epimerase; T6PP, tagatose 6-phosphate phosphatase.
Figure 5:
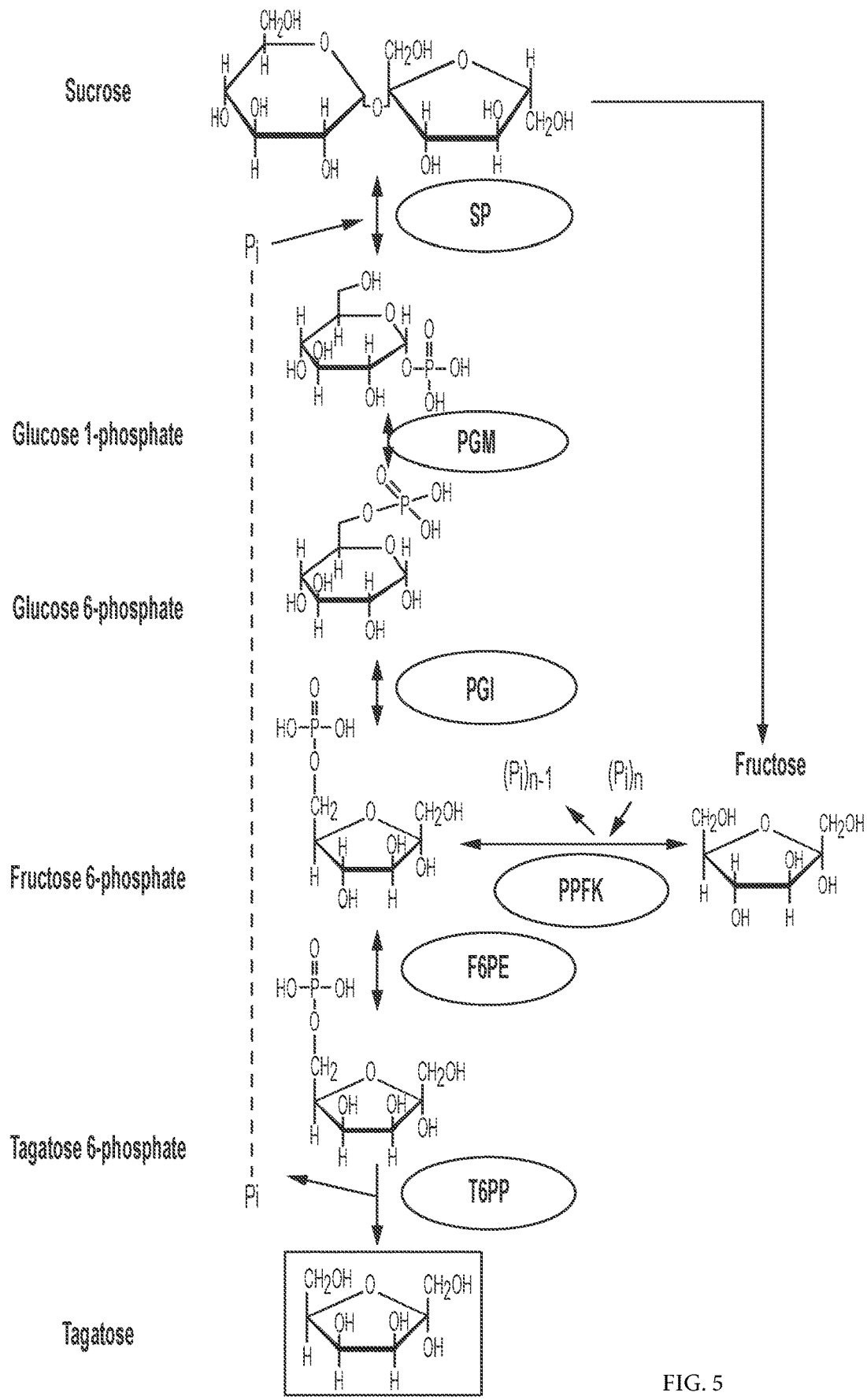
FIG. 5 shows an enzymatic pathway converting sucrose or its derived products to tagatose. SP, sucrose phosphorylase; PPFK, polyphosphate fructokinase; PGM, phosphoglucomutase; PGI, phosphoglucoisomerase; F6PE, fructose 6-phosphate epimerase; T6PP, tagatose 6-phosphate phosphatase.

Additionally, the processes according to the invention may further comprise the step of converting a saccharide to the G1P, where the step is catalyzed by at least one enzyme, and the saccharide is selected from the group consisting of a starch or derivative thereof (FIG. 1), cellulose or a derivative thereof (FIG. 2), fructose (FIG. 3), glucose (FIG. 4), and sucrose (FIG. 5). The enzyme or enzymes used in the step of converting a saccharide to the G1P in the processes according to the invention can be alpha-glucan phosphorylase (αGP), maltose phosphorylase, sucrose phosphorylase, cellodextrin phosphorylase, cellobiose phosphorylase, and/or cellulose phosphorylase, and mixtures thereof. The choice of the enzyme or enzyme combination to arrive at F6P depends on the saccharide used in the process.

Cellulose is the most abundant bio resource and is the primary component of plant cell walls. Non-food lignocellulosic biomass contains cellulose, hemicellulose, and lignin as well as other minor components. Pure cellulose, including Avicel (microcrystalline cellulose), regenerated amorphous cellulose, bacterial cellulose, filter paper, and so on, can be prepared via a series of treatments. The partially hydrolyzed cellulosic substrates include water-insoluble cellodextrins whose degree of polymerization is more than 7, water-soluble cellodextrins with degree of polymerization of 3-6, cellobiose, glucose, and fructose.

In certain processes according to the invention, cellulose and its derived products can be converted to tagatose through a series of steps. See FIG. 2. For example, a process according to the invention provides a pathway that involves the following steps: generating G1P from cellodextrin and cellobiose and free phosphate catalyzed by cellodextrin phosphorylase (CDP) and cellobiose phosphorylase (CBP), respectively; converting G1P to G6P catalyzed by PGM; converting G6P to F6P catalyzed by PGI; converting F6P to tagatose as described above, and the phosphate ions can be recycled by the step of converting cellodextrin and cellobiose to G1P.

Several enzymes may be used to hydrolyze solid cellulose to water-soluble cellodextrins and cellobiose. Such enzymes include endoglucanase and cellobiohydrolase, but not including beta-glucosidase (cellobiase). Prior to cellulose hydrolysis and G1P generation, cellulose and biomass can be pretreated to increase their reactivity and decrease the degree of polymerization of cellulose chains. Cellulose and biomass pretreatment methods include dilute acid pretreatment, cellulose solvent-based lignocellulose fractionation, ammonia fiber expansion, ammonia aqueous soaking, ionic liquid treatment, and partially hydrolyzed by using concentrated acids, including hydrochloric acid, sulfuric acid, phosphoric acid and their combinations.

When the saccharides include cellobiose, and the enzymes contain cellobiose phosphorylase, G1P is generated from cellobiose by cellobiose phosphorylase. When the saccharides contain cellodextrins and the enzymes include cellodextrin phosphorylase, G1P is generated from cellodextrins by cellodextrin phosphorylase. When the saccharides include cellulose, and enzymes contain cellulose phosphorylase, the G1P is generated from cellulose by cellulose phosphorylase.

When the saccharides include maltose and the enzymes contain maltose phosphorylase, the G1P is generated from maltose by maltose phosphorylase. If the saccharides include sucrose, and enzymes contain sucrose phosphorylase, the G1P is generated from sucrose by sucrose phosphorylase.

When the saccharide is starch or a starch derivative, the derivative may be selected from the group consisting of amylose, amylopectin, soluble starch, amylodextrin, maltodextrin, maltose, maltotriose, and glucose, and mixtures thereof. In certain processes of the invention, the enzymes used to convert a saccharide to G1P contain αGP. In this step, when the saccharides include starch, the G1P is generated from starch by αGP; when the saccharides contain soluble starch, amylodextrin, or maltodextrin, the G1P is produced from soluble starch, amylodextrin, or maltodextrin by αGP. An example of αGP is αGP from *Thermotoga maritima* (Uniprot ID G4FEH8), disclosed in International Patent Application Publication WO2017/059278.

Some processes according to the invention may further comprise the step of converting starch to a starch derivative, where the starch derivative is prepared by enzymatic hydrolysis of starch or by acid hydrolysis of starch. In certain processes of the invention, maltose phosphorylase (MP) can be used to increase tagatose yields by phosphorolytically cleaving the degradation product maltose into G1P and glucose. Alternatively, 4-glucan transferase (4GT) can be used to increase tagatose yields by recycling the degradation products glucose, maltose, and maltotriose into longer maltooligosaccharides; which can be phosphorolytically cleaved by αGP to yield G1P. An example of 4GT is 4GT from *Thermococcus litoralis* (Uniprot ID 032462), disclosed in International Patent Application Publication WO2017/059278. In some processes of the invention, polyphosphate and polyphosphate glucokinase (PPGK) can be added to the process, thus increasing yields of tagatose by phosphorylating the degradation product glucose to G6P.

Starch is the most widely used energy storage compound in nature and is mostly stored in plant seeds. Natural starch contains linear amylose and branched amylopectin. Examples of starch derivatives include amylose, amylopectin, soluble starch, amylodextrin, maltodextrin, maltose, fructose, and glucose. Examples of cellulose derivatives include pretreated biomass, regenerated amorphous cellulose, cellodextrin, cellobiose, fructose, and glucose. Sucrose derivatives include fructose and glucose.

Where the processes use a starch derivative, the starch derivative can be prepared by enzymatic hydrolysis of starch catalyzed by isoamylase, pullulanase, α-amylase, or their combination. Corn starch contains many branches that impede αGP action. Isoamylase can be used to de-branch starch, yielding linear amylodextrin. Isoamylase-pretreated starch can result in a higher F6P concentration in the final product. Isoamylase and pullulanase cleave alpha-1,6-glycosidic bonds, which allows for more complete degradation of starch by alpha-glucan phosphorylase. Alpha-amylase cleaves alpha-1,4-glycosidic bonds, therefore alpha-amylase is used to degrade starch into fragments for quicker conversion to tagatose.

Tagatose can also be produced from fructose. See FIG. 3. Processes according to the inventions can also comprise the step of converting fructose to F6P, wherein the step is catalyzed by at least one enzyme and, optionally, the step of converting sucrose to the fructose, wherein the step is catalyzed by at least one enzyme. For example, the process involves generating F6P from fructose and polyphosphate catalyzed by polyphosphate fructokinase (PPFK). The conversion of F6P to tagatose is described above. The fructose can be produced, for example, by an enzymatic conversion of sucrose. The phosphate ions generated when T6P is converted to tagatose can then be recycled in the steps of converting sucrose to G1P.

Tagatose can also be produced from glucose. See FIG. 4. Processes according to the inventions can also comprise the step of converting glucose to G6P, catalyzed by at least one enzyme, and, optionally, the step of converting sucrose to the fructose, wherein the step is catalyzed by at least one enzyme. For example, the process involves generating G6P from glucose and polyphosphate catalyzed by polyphosphate glucokinase (PPGK). The glucose can be produced, for example, by an enzymatic conversion of sucrose. See FIG. 5.

In some methods of the invention, the phosphate ions generated when T6P is converted to tagatose are recycled in the step of converting starch derivatives to G1P (See, e.g., FIG. 1), cellulose derivatives to G1P (See e.g., FIG. 2), or sucrose to G1P (See FIG. 5), especially if the process is conducted in a single reaction vessel. Additionally, PPFK and polyphosphate can be used to increase tagatose yields by producing F6P from fructose generated by the phosphorolytic cleavage of sucrose by SP.

Processes for preparing tagatose from a saccharide, for example, include the following steps: (i) converting a saccharide to glucose 1-phosphate (G1P) using one or more enzymes; (ii) converting G1P to G6P using phosphoglucomutase (PGM, EC 5.4.2.2); (iii) converting G6P to F6P using phosphoglucoisomerase (PGI, EC 5.3.1.9); (iv) converting F6P to T6P via fructose 6-phosphate epimerase (F6PE), and (v) converting T6P to tagatose via tagatose 6-phosphate phosphatase (T6PP). In improved processes of the invention, the F6PE comprises an amino acid sequence having at least 90% sequence identity to SEQ ID NO: 1, SEQ ID NO: 2, or SEQ ID NO: 7, and/or the T6PP comprises an amino acid sequence having at least 90% sequence identity to SEQ ID NO: 3, SEQ ID NO: 4, SEQ ID NO: 5, or SEQ ID NO: 6. In such processes, for example, the enzyme in step (i) is αGP. Typically, the ratios of enzyme units used in the process are 1:1:1:1:1 (αGP:PGM:PGI:F6PE:T6PP). An enzyme unit is the amount of enzyme needed to convert 1 umol of substrate to product in 1 minute. Accordingly, an enzyme with a higher activity will have a lower amount of enzyme, in terms of mg of enzyme per one enzyme unit, compared to an enzyme with a lower activity which catalyzes the same reaction. To optimize product yields, these ratios can be adjusted in any number of combinations. For example, a particular enzyme may be present in an amount about 2x, 3x, 4x, 5x, etc. relative to the amount of other enzymes.

A process for preparing tagatose according to the invention may include the following additional steps: generating glucose from polysaccharides and oligosaccharides by enzymatic hydrolysis or acid hydrolysis, converting glucose to G6P catalyzed by at least one enzyme, generating fructose from polysaccharides and oligosaccharides by enzymatic hydrolysis or acid hydrolysis, and converting fructose to G6P catalyzed by at least one enzyme. Examples of the polysaccharides and oligosaccharides are enumerated above.

Processes to prepare tagatose according the invention can be conducted in a single bioreactor or reaction vessel. Alternatively, the steps can also be conducted in a plurality of bioreactors, or reaction vessels, that are arranged in series. In a preferred process, the enzymatic production of tagatose is conducted in a single reaction vessel.

The enzymes used in the invention may take the form of soluble, immobilized, assembled, or aggregated proteins. These enzymes could be adsorbed on insoluble organic or inorganic supports commonly used to improve functionality, as known in the art. These include polymeric supports such as agarose, methacrylate, polystyrene, or dextran, as well as inorganic supports such as glass, metal, or carbon-based materials. These materials are often produced with large surface-to-volume ratios and specialized surfaces that promote attachment and activity of immobilized enzymes. The enzymes might be affixed to these solid supports through covalent, ionic, or hydrophobic interactions. The enzymes could also be affixed through genetically engineered interactions such as covalent fusion to another protein or peptide sequence with affinity to the solid support, most often a poly-histidine sequence. The enzymes might be affixed either directly to the surface or surface coating, or they might be affixed to other proteins already present on the surface or surface coating. The enzymes can be immobilized all on one carrier, on individual carriers, or a combination of the two (e.g., two enzyme per carrier then mix those carriers). These variations can be mixed evenly or in defined layers to optimize turnover in a continuous reactor. For example, the beginning of the reactor may have a layer of αGP to ensure a high initial G1P increase. Enzymes may be immobilized all on one carrier, on individual carriers, or in groups. These enzymes may be mixed evenly or in defined layers or zones to optimize turnover.

Any suitable biological buffer known in the art can be used in a process of the invention, such as HEPES, PBS, BIS-TRIS, MOPS, DIPSO, Trizma, etc. The reaction buffer for all embodiments can have a pH ranging from 5.0-9.0. More preferably, the reaction buffer pH can range from about 6.0 to about 7.3. For example, the reaction buffer pH can be 6.0, 6.2, 6.4, 6.6, 6.8, 7.0, 7.2, or 7.3.

In some improved processes of the invention the reaction buffer contains divalent metal cations. Examples include $Mn^{2+}$, $Co^{2+}$, $Mg^{2+}$ and $Zn^{2+}$, and the like, preferably $Mg^{2+}$ The concentration of divalent metal cations can range from about 0 mM to about 150 mM, from about 0 mM to about 100 mM, from about 1 mM to about 50 mM, preferably from about 5 mM to about 50 mM, or more preferably from about 10 mM to about 50 mM. For instance, the divalent metal cation concentration can be about 0.1 mM, about 0.5 mM, about 1 mM, about 1.5 mM, about 2 mM, about 2.5 mM, about 5 mM, about 6 mM, about 7 mM, about 8 mM, about 9 mM, about 10 mM, about 15 mM, about 20 mM, about 25 mM, about 30 mM, about 35 mM, about 40 mM, about 45 mM, about 50 mM, or about 55 mM.

The reaction temperature at which the process steps are conducted can range from 37–85° C. More preferably, the steps can be conducted at a temperature ranging from about 37° C. to about 85° C. The temperature can be, for example, about 40° C., about 45° C., about 50° C., about 55° C., or about 60° C. Preferably, the reaction temperature is about 50° C. In some processes of the invention, the reaction temperature is constant, and is not changed during the process.

The reaction time of the disclosed processes can be adjusted as necessary and can range from about 1 hour to about 48 hours. For example, the reaction time can be about 16 hours, about 18 hours, about 20 hours, about 22 hours, about 24 hours, about 26 hours, about 28 hours, about 30 hours, about 32 hours, about 34 hours, about 36 hours, about 38 hours, about 40 hours, about 42 hours, about 44 hours, about 46 hours, or about 48 hours. More preferably, the reaction time is about 24 hours.

The reaction can be run in batch or in a continuous process using a packed bed reactor or similar device. In the continuous process, a solution maltodextrin would be pumped through a bed of immobilized enzyme at such a rate that conversion to tagatose would be complete when the solution leaves the column for downstream processing. For example, 200 g/L of maltodextrin can be pumped through a column packed with immobilized enzymes (maintained at, for example, 50° C.) such that when the maltodextrin leaves the column maximum tagatose yield is achieved. This methodology offers greater volumetric productivity over batch methods. This limits the time our product is in contact with the column and reaction conditions, which decreases chances of product degradation (e.g., potential hydroxymethylfurfural formation). Whether in batch or continuous mode the various steps of processes of the invention may be conducted using the same reaction conditions as the other steps. For example, in a particular process of the invention using a single bioreactor or reaction vessel, the reaction conditions such as pH and temperature, and reaction buffer are kept constant for all steps of the process.

Phosphate ions produced by T6PP dephosphorylation of T6P can then be recycled in the process step of converting a saccharide to G1P, particularly when all process steps are conducted in a single bioreactor or reaction vessel. The ability to recycle phosphate in the disclosed processes allows for non-stoichiometric amounts of phosphate to be used, which keeps reaction phosphate concentrations low. This affects the overall pathway and the overall rate of the processes, but does not limit the activity of the individual enzymes and allows for overall efficiency of the tagatose making processes.

For example, reaction phosphate concentrations can range from about 0 mM to about 300 mM, from about 0 mM to about 150 mM, from about 1 mM to about 50 mM, preferably from about 5 mM to about 50 mM, or more preferably from about 10 mM to about 50 mM. For instance, the reaction phosphate concentration can be about 0.1 mM, about 0.5 mM, about 1 mM, about 1.5 mM, about 2 mM, about 2.5 mM, about 5 mM, about 6 mM, about 7 mM, about 8 mM, about 9 mM, about 10 mM, about 15 mM, about 20 mM, about 25 mM, about 30 mM, about 35 mM, about 40 mM, about 45 mM, about 50 mM, or about 55 mM.

Therefore, low phosphate concentrations result in decreased production costs due to low total phosphate and thus lowered cost of phosphate removal. It also prevents inhibition of T6PP by high concentrations of free phosphate and decreases the potential for phosphate pollution.

Figure 6:
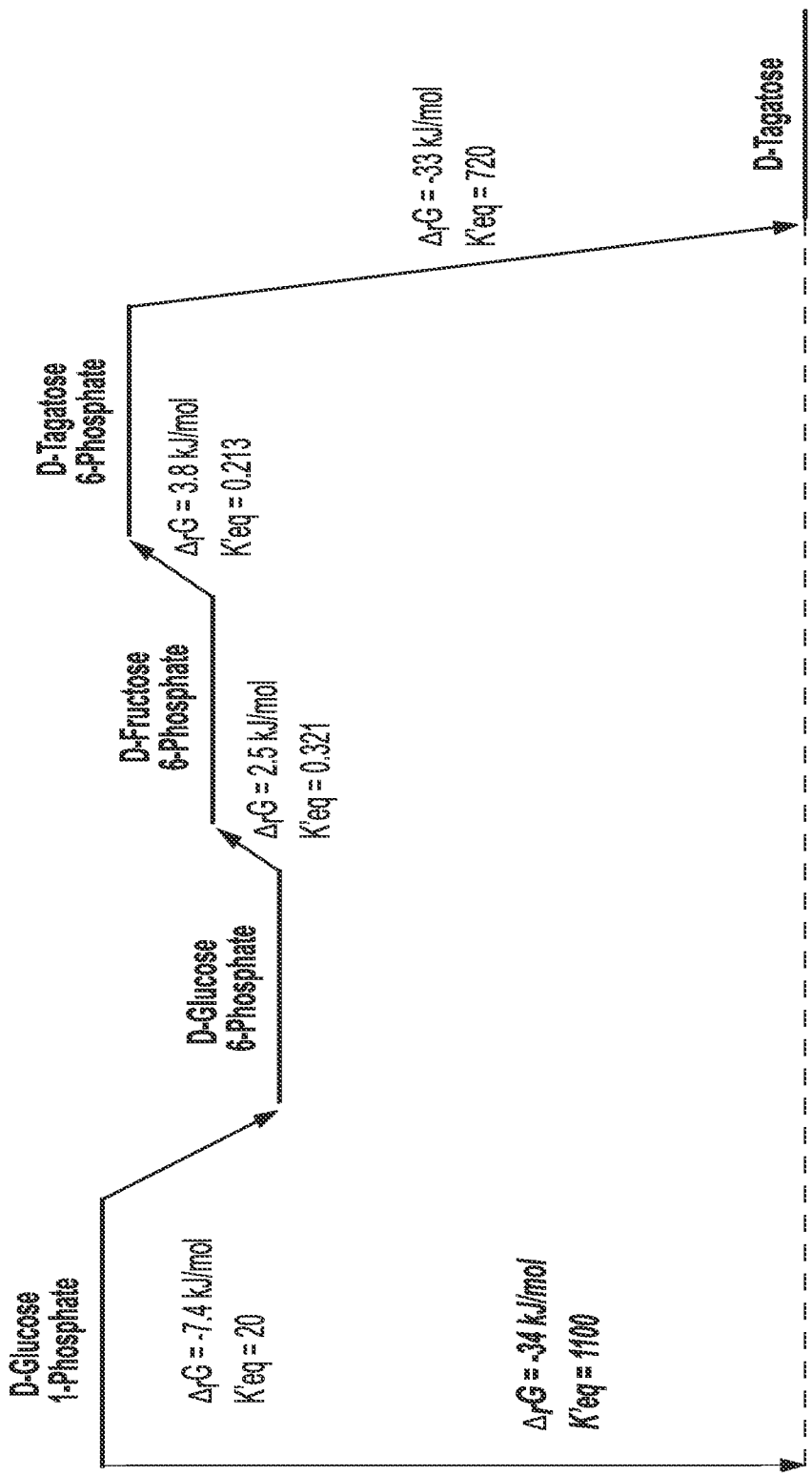
FIG. 6 shows the Reaction Gibbs Energy between intermediates based on formation Gibbs energy for the conversion of glucose 1-phosphate to tagatose.

Furthermore, the processes disclosed herein can be conducted without added ATP as a source of phosphate, i.e., ATP-free. The processes can also be conducted without having to add NAD(H), i.e., NAD(H)-free. Other advantages also include the fact that at least one step of the disclosed processes for making tagatose involves an energetically favorable chemical reaction. FIG. 6. While the use of enzymes with higher activities will not affect the overall energetics, the ability to use lower amounts of enzymes in the improved processes is advantageous. The advantage is the reduction of the overall cost of enzyme in the total production cost of the product.

The processes according to the invention can achieve high yields due to the very favorable equilibrium constant for the overall reaction. Theoretically, up to 99% yields can be achieved if the starting material is completely converted to an intermediate. Also, the step of converting T6P to tagatose according to the invention is an irreversible phosphatase reaction, regardless of the feedstock. Therefore, tagatose is produced with a very high yield.

Processes of the invention use low-cost starting materials and reduce production costs by decreasing costs associated with the feedstock and product separation. Starch, cellulose, sucrose and their derivatives are less expensive feedstocks than, for example, lactose. When tagatose is produced from lactose, glucose and galactose and tagatose are separated via chromatography, which leads to higher production costs.

Processes according to the invention allow for easy recovery of tagatose, and separation costs are minimized. Preferably, in processes of the invention, the recovery of tagatose is not via chromatographic separation. Following production of tagatose in a continuous reaction, the product is instead passed through microfiltration, ion exchange (cation then anion, not mixed bed), concentration, crystallization, crystal isolation, and drying. Due to high yields of tagatose, the crystallization step is all that is needed to purify tagatose. To further purify tagatose prior to crystallization, one can employ nanofiltration to eliminate the risk of enzyme being present in the crystallization process and to remove any unconverted dextrins that may co-crystallize with tagatose or limit the recyclability of the mother liquor (maltodextrin, maltotetraose, maltotriose, maltose, etc.).

An improved process for preparing tagatose according to the invention includes the following steps: (i) converting a saccharide to glucose 1-phosphate (G1P) using one or more enzymes; (ii) converting G1P to G6P using phosphoglucomutase (PGM, EC 5.4.2.2); (iii) converting G6P to F6P using phosphoglucoisomerase (PGI, EC 5.3.1.9); (iv) converting F6P to T6P via fructose 6-phosphate epimerase (F6PE), and (v) converting T6P to tagatose via tagatose 6-phosphate phosphatase (T6PP), where the F6PE comprises an amino acid sequence having at least 90% sequence identity to SEQ ID NO: 1, SEQ ID NO: 2, or SEQ ID NO: 7, and/or where the T6PP comprises an amino acid sequence having at least 90% sequence identity to SEQ ID NO: 3, SEQ ID NO: 4, SEQ ID NO: 5, or SEQ ID NO: 6. This process is preferably conducted in a single bioreactor or reaction vessel.

Preferably, an improved process for preparing tagatose according to the invention includes the following steps: (i) converting a saccharide to glucose 1-phosphate (G1P) using αGP, where the saccharide is selected from the group consisting of starch, one or more derivatives of starch, or a combination thereof; (ii) converting G1P to G6P using phosphoglucomutase (PGM, EC 5.4.2.2); (iii) converting G6P to F6P using phosphoglucoisomerase (PGI, EC 5.3.1.9); (iv) converting F6P to T6P via fructose 6-phosphate epimerase (F6PE), and (v) converting T6P to tagatose via tagatose 6-phosphate phosphatase (T6PP), where the F6PE comprises an amino acid sequence having at least 90% sequence identity to SEQ ID NO: 1, SEQ ID NO: 2, or SEQ ID NO: 7, and/or where the T6PP comprises an amino acid sequence having at least 90% sequence identity to SEQ ID NO: 3, SEQ ID NO: 4, SEQ ID NO: 5, or SEQ ID NO: 6. The process is preferably conducted in a single reactor vessel and may incorporate one or more of the various process conditions discussed above.

EXAMPLES

Materials and Methods

All chemicals, including glucose 1-phosphate, magnesium chloride, sodium phosphate (mono and dibasic), are reagent grade or higher and purchased from Sigma-Aldrich (St. Louis, MO, USA) or Fisher Scientific (Pittsburgh, PA, USA), unless otherwise noted. E. coli BL21 (DE3) (Sigma-Aldrich, St. Louis, MO, USA) was used as a host cell for recombinant protein expression. ZYM-5052 media including 50 mg L-1 kanamycin was used for E. coli cell growth and recombinant protein expression.

Production and Purification of Recombinant Enzymes

The E. coli BL21 (DE3) strain harboring a protein expression plasmid (pET28a) was incubated in a 1-L Erlenmeyer flask with 100 mL of ZYM-5052 media containing 50 mg $L^{-1}$ kanamycin. Cells were grown at 37° C. with rotary shaking at 220 rpm for 16-24 hours. The cells were harvested by centrifugation at 12° C. and washed once with either 20 mM HEPES (pH 7.5) containing 50 mM NaCl and 5 mM $MgCl_2$ (heat precipitation) or 20 mM HEPES (pH 7.5) containing 300 mM NaCl and 5 mM imidazole (Ni purification). The cell pellets were re-suspended in the same buffer and lysed by sonication. After centrifugation, the target proteins in the supernatants were purified. His-tagged proteins were purified by the Profinity IMAC Ni-Charged Resin (Bio-Rad, Hercules, CA, USA). Heat precipitation at 50-80° C. for 5-30 min was used to purify thermostable enzymes. The purity of the recombinant proteins was examined by sodium dodecyl sulfate polyacrylamide gel electrophoresis (SDS-PAGE).

Example 1: F6PEs with Higher Activity

The relative activities of different F6PEs were measured in 50 mM HEPES buffer (pH 7.2) containing 5 mM $MgCl_2$, 0.5 mM $MnCl_2$, 38.5 mM G1P, 0.05 g/L PGM, 0.05 g/L PGI, 0.05 g/L F6PE, and 0.075 g/L T6PP from Methanosarcina thermophila CHTI-55 (Uniprot ID A0A0E3NCH4) at 50° C. for 1 hour. The reaction was stopped via filtration of enzyme with a Vivaspin 2 concentrator (10,000 MWCO). The product, tagatose, was evaluated using an Agilent Hi-Plex H-column and refractive index detector. The sample was run in 5 mM $H_2SO_4$ at 0.6 mL/min for 15 min at 65° C. Table 1 shows that F6PEs used in the improved processes of the invention have higher activity relative to the previously disclosed F6PE from Dictyoglomus thermophilum (Uniprot ID B5YBD7). See International Patent Application Publication WO2017/059278.

TABLE 1

| Relative activities of F6PEs | |
|---|---|
| F6PE (Uniprot ID) | Relative activity (%) |
| B5YBD7 (Comparative) | 100 |
| A0A0P6XN50 (SEQ ID NO: 1) | 250 |
| A0A223HVJ3 (SEQ ID NO: 2) | 278 |
| A0A2M8QBR9 (SEQ ID NO: 7) | 220 |

Example 2: T6PPs with Higher Activity

The relative activities of T6PPs were measured in 50 mM HEPES buffer (pH 7.2) containing 5 mM $MgCl_2$, 0.5 mM $MnCl_2$, 38.5 mM G1P, 0.05 g/L PGM, 0.05 g/L PGI, 0.25 g/L F6PE from Thermanaerothrix daxensis (Uniprot ID A0A0P6XN50), and 0.05 g/L T6PP at 50° C. for 1 hour. The reaction was stopped via filtration of enzyme with a Vivaspin 2 concentrator (10,000 MWCO). The product, tagatose, was evaluated using an Agilent Hi-Plex H-column and refractive index detector. The sample was run in 5 mM $H_2SO_4$ at 0.6 mL/min for 15 min at 65° C. Table 2 shows that T6PPs used in the improved processes of the invention have higher activity relative to the previously disclosed T6PP from Archaeoglobus fulgidus (Uniprot ID O29805). See International Patent Application Publication WO 2017/059278.

TABLE 2

| Relative activities of T6PP | |
|---|---|
| T6PP Uniprot ID | Relative activity (%) |
| O29805 (Comparative) | 100 |
| A0A0E3NCH4 (SEQ ID NO: 3) | 714 |
| D6YBK5 (SEQ ID NO: 4) | 1428 |
| E0RT70 (SEQ ID NO: 5) | 2175 |
| D1C7G9 (SEQ ID NO: 6) | 914 |

Example 3: Improved Tagatose Production from F6P

The conversion of F6P to tagatose using previously disclosed enzymes, F6PE (Uniprot ID B5YBD7) and T6PP (Uniprot ID O29805), was compared with the conversion of F6P to tagatose with enzymes useful in the improved processes of the invention, F6PE (Uniprot ID A0A0P6XN50) and T6PP (Uniprot ID D6YBK5). A 0.20 mL reaction mixture containing 38.5 mM F6P, 50 mM HEPES pH 7.2, 5 mM $MgCl_2$, 0.5 mM $MnCl_2$, 0.1 g/L F6PE, and 0.033 g/L T6PP was incubated at 50° C. for 2 hours.

Figure 7:
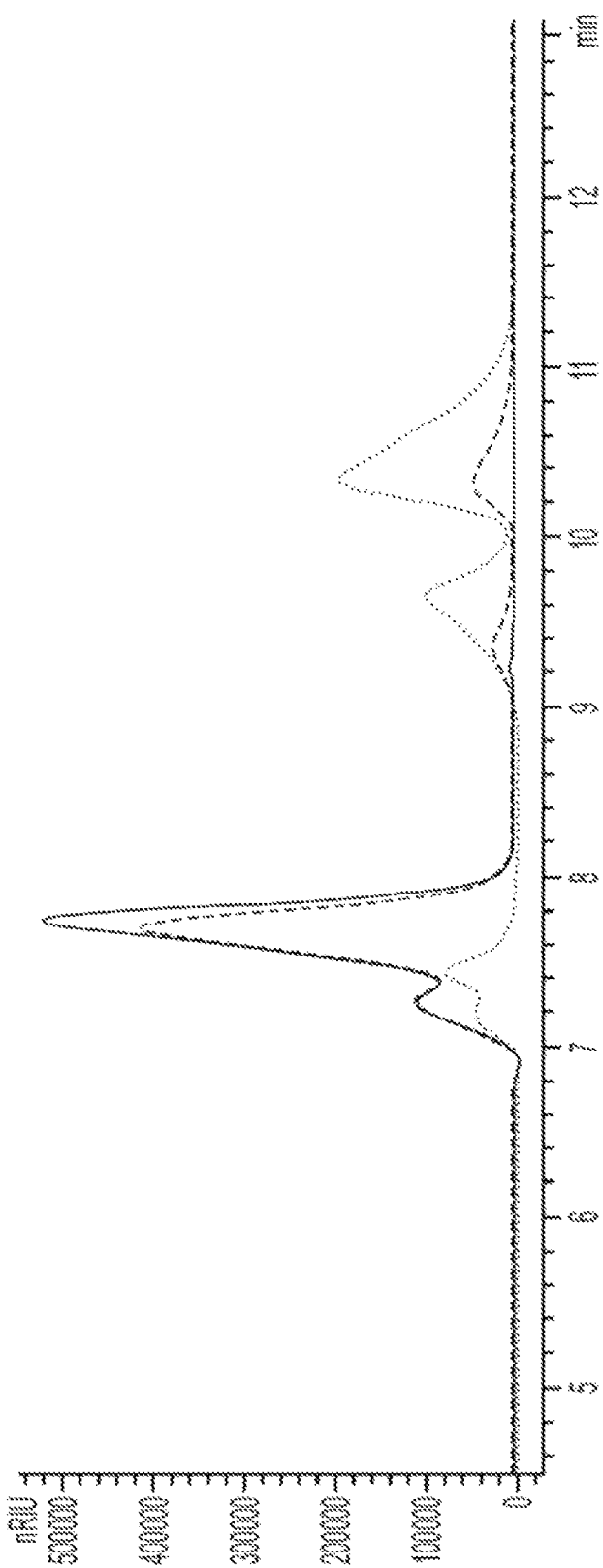
FIG. 7 shows the conversion of F6P to tagatose as described in Example 3 in an HPLC chromatogram. (solid line) 0 hour chromatogram; (dashed line) 2 hour with F6PE (Uniprot ID B5YBD7) and T6PP (Uniprot ID O29805); and (dotted line) 2 hour with the improved process with F6PE (Uniprot ID A0A0P6XN50) and T6PP (Uniprot ID D6YBK5); peaks shown are (1) Void, (2) F6P and T6P, (3) free phosphate, (4) tagatose, and (5) fructose.

The reaction was stopped via filtration of enzyme with a Vivaspin 2 concentrator (10,000 MWCO) and analyzed via HPLC (Agilent 1100 series) using an Agilent Hi-Plex H-column and refractive index detector. The sample was run in 5 mM $H_2SO_4$ at 0.6 mL/min for 15.5 minutes at 65° C. Results show a 4.4-fold improvement in tagatose production with the enzymes of the improved process over the previously disclosed enzymes (FIG. 7). A slight amount of fructose (see FIG. 7, shoulder, 5, on peak 4) is present in the reaction with the enzymes of the improved process. This may be an artifact due to the T6PP initially seeing a large abundance of F6P compared to T6P for the reaction here and is not an issue in the full pathway.

Sequence Listing

Alpha-glucan phosphorylase

*Thermotoga maritima* (Uniprot ID G4FEH8) - SEQ ID NO: 8
```
MLEKLPENLKELESLAYNLWWSWSRPAQRLWRMIDSEKWEEHRNPVKILREVSKERLEELSKDEDFIALYELTLERFTDY
MEREDTWFNVNYPEWDEKIVYMCMEYGLTKALPIYSGGLGILAGDHLKSASDLGLPLIAVGLLYKHGYFTQQIDSDGR
QIEIFPEYDIEELPMKPLRDEDGNQVIVEVPIDNDTVKARVFEVQVGRVKLYLLDTDFEENEDRFRKICDYLYNPEPDVRV
SQEILLGIGGMKLLKTLKIKPGVIHLNEGHPAFSSLERIKSYMEEGYSFTEALEIVRQTTVFTTHTPVPAGHDRFPFDFVEKK
LTKFFEGFESKELLMNLGKDEDGNFNMTYLALRTSSFINGVSKLHADVSRRMFKNVWKGVPVEEIPIEGITNGVHMGT
WINREMRKLFDRYLGRVWREHTDLEGIWYGVDRIPDEELWEAHLNAKKRFIDYIRESIKRRNERLGINEPLPEISENVLII
GFARRFATYKRAVLLFSDLERLKRIVNNSERPVYIVYAGKAHPRDEGGKEFLRRIYEVSQMPDFKNKIIVLENYDIGMARL
MVSGVDVWLNNPRRPMEASGTSGMKAAANGVLNASVYDGWWVEGYNGRNGWVIGDESVLPETEADDPKDAEAL
YELLENEIIPTYYENREKWIFMMKESIKSVAPKFSTTRMLKEYTEKFYIKGLVNREWLERRENVEKIGAWKERILKNWENV
SIERIVLEDSKSVEVTVKLGDLTPNDVIVELVAGRGEGMEDLEVWKVIHIRRYRKENDLFVYTYTNGVLGHLGSPGWFYA
VRVIPYHPRLPIKFLPEVPVVWKKVL
```

Phosphoglucomutase

*Thermococcus kodakaraensis* (Uniprot ID Q68I3J6) - SEQ ID NO: 9
```
MGKLFGTFGVRGIANEEITPEFALKIGMAFGTLLKREGRERPLVVVGRDTRVSGEMLKDALISGLLSTGCDVIDVGIAPTP
AIQWATNHFNADGGAVITASHNPPEYNGIKLLEPNGMGLKKEREAIVEELFFSEDFHRAKWNEIGELRKEDIIKPYIEAIK
NRVDVEAIKKRRPFVVVDTSNGAGSLTLPYLLRELGCKVVSVNAHPDGHFPARNPEPNEENLKGFMEIVKALGADFGV
AQDGDADRAVFIDENGRFIQGDKTFALVADAVLRENGGGLLVTTIATSNLLDDIAKRNGAKVMRTKVGDLIVARALLEN
NGTIGGEENGGVIFPDFVLGRDGAMTTAKIVEIFAKSGKKFSELIDELPKYYQFKTKRHVEGDRKAIVAKVAELAEKKGYKI
DTTDGTKIIFDDGWVLVRASGTEPIIRIFSEAKSEEKAREYLELGIKLLEEALKG
```

Fructose 6-phosphate 4-epimerases (Comparative) *Dictyoglomus thermophilum* (Uniprot ID B5YBD7) - SEQ ID NO: 10
```
MWLSKDYLRKKGVYSICSSNPYVIEASVEFAKEKNDYILIEATPHQINQFGGYSGMTPEDFKNFVMGIIKEKGIEEDRVIL
GGDHLGPLPWQDEPSSSAMKKAKDLIRAFVESGYKKIHLDCSMSLSDDPVVLSPEKIAERERELLEVAEETARKYNFQPV
YVVGTDVPVAGGGEEEGITSVEDFRVAISSLKKYFEDVPRIWDRIIGFVIMLGIGFNYEKVFEYDRIKVRKILEEVKKENLFV
EGHSTDYQTKRALRDMVEDGVRILKVGPALTASFRRGVFLLSSIEDELISEDKRSNIKKVVLETMLKDDKYWRKYYKDSER
LELDIWYNLLDRIRYYWEYKEIKIALNRLFENFSEGVDIRYIYQYFYDSYFKVREGKIRNDPRELIKNEIKKVLEDYHYAVNL
```

*Thermanaerothrix daxensis* (Uniprot ID A0A0P6XN50) - SEQ ID NO: 1
```
MVTYLDFVVLSHRFRRPLGITSVCSAHPYVIEAALRNGMMTHTPVLIEATCNQVNQYGGYTGMTPADFVRYVENIAAR
VGSPRENLLLGGDHLGPLVWAHEPAESAMEKARALVKAYVEAGFRKIHLDCSMPCADDRDFSPKVIAERAAELAQVAE
STCDVMGLPLPNYVIGTEVPPAGGAKAEAETLRVTRPEDAAETIALTRAAFFKRGLESAWERVVALVVQPGVEFGDHQI
HVYRREEAQALSRFIESQPGLVYEAHSTDYQPRDALRALVEDHFAILKVGPALTFAFREAVFALASIEDWVCDSPSRILEV
LETTMLANPVYWQKYYLGDERARRIARGYSFSDRIRYYWSAPAVEQAFERLRANLNRVSIPLVLLSQYLPDQYRKVRDG
RLPNQFDALILDKIQAVLEDYNVACGVRIGE
```

*Thermoanaerobacterium thermosaccharolyticum* (Uniprot ID A0A223HVJ3) - SEQ ID NO: 2
```
MAKEHPLKELVNKQKSGISEGIVSICSSNEFVIEASMERALTNGDYVLIESTANQVNQYGGYIGMTPIEFKKFVFSIAKKV
DFPLDKLILGGDHLGPLIWKNESSNLALAKASELIKEYVLAGYTKIHIDTSMRLKDDTDFNTEIIAQRSAVLLKAAENAYME
LNKNNKNVLHPVYVIGSEVPIPGGSQGSDESLQITDAKDFENTVEIFKDVFSKYGLINEWENIVAFVVQPGVEFGNDFVH
EYKRDEAKELTDALKNYKTFVFEGHSTDYQTRESLKQMVEDGIAILKVGPALTFALREALIALNNIENELLNNVDSIKLSNF
TNVLVSEMINNPEHWKNHYFGDDARKKFLCKYSYSDRCRYYLPTRNVKNSLNLLIRNLENVKIPMTLISQFMPLQYDNIR
RGLIKNEPISLIKNAIMNRLNDYYYAIKP
```

*Candidatus Thermofonsia* Clade 3 bacterium (Uniprot ID A0A2M8QBR9) - SEQ ID NO: 7
```
MTYLDYLTASHHSGKPIGLSSICSAHPWVLRTALQGERPVLIESTCNQVNQFGGYSGMKPADFVRFVHSLAAENGFPTE
KILLGGDHLGPSPWQNEPAEQAMAKAIEMVRAYVQAGYTKIHLDCSMPLGGERQLPVEVIAQRTVQLAEAAEQAAHE
SRLTSHTLRYVIGSEVPPPGGAIGPHEGLRVTPVEEARQTLEVMQAAFHQAGLEAAWERVRALVVQPGVEFGDDFVH
DYDPAAAAGLARFIETVPNLVYEAHSTDYQTPESLAALVRDHFAILKVGPALTFALREAVFALAMIENELFPAEERSHLVE
RLEAAMLRQPGHWQRHYHGEERQQALARKYSFSDRIRYYWGDPDVQAAFRQLLANLERVAPLPLTLLSQYLPEMFGE
IRRGLLLNHPAAFLERKIQAVLDTYRAACGEED
```

Tagatose 6-phosphate phosphatases (Comparative) *Archaeoglobus fugidis* (Uniprot ID O29805) - SEQ ID NO: 11
```
MFPKPKAIAVDIDGTLTLDRKRALNCRAVEALRKVKIPVILATGNISCFARAAAKLIGVSDVVICENGGVVRFEYDGEDIVLG
DKEKCVEAVRVLEKHYEVELLDFEYRKSEVCMRRSFDINEARKLIEGMGVKLVDSGFAYHIMDADVSKGKALKFVAERL
GISSAEFAVIGDSENDIDMFRVAGFGIAVANADERLKEYADLVTPSPDGEGVVEALQFLGLLR
```

*Methanosarcina thermophila* CHTI-55 (Uniprot ID A0A0E3NCH4) - SEQ ID NO: 3
```
MLKALIFDMDGVLVDSMPFHAAAWKKAFFEMGMEIQDSDIFAIEGSNPRNGLPLLIRKARKEPEAFDFEAITSIYRQEFK
RVFEPKAFEGMKECLEVLKKRFLLSVVSGSDHVIVHSIINRLFPGIFDIVVTGDDIINSKPHPDPFLKAVELLNVRREECVVIE
NAILGVEAAKNARIYCIGVPTYVEPSHLDKADLVVEDHRQLMQHLLSLEPANGFRQ
```

*Thermobispora bispora* strain ATCC 19993 (Uniprot ID D6Y13K5) - SEQ ID NO: 4
```
MDVVLFDMDGLLVDTERLWFAVETEVVERLGGSWGPEHQRQLVGGSLKRAVAYMLEHTGADVDPDVVAGWLIEG
MERRLTESVDPMPGAMELLTALRDEGIPTGLVTSSRRPLADAVLKHIGREHFDVVVTADDVSHAKPHPEPYLTALAMLS
ADPARSVALEDSPNGVASAVAAGCRVVAVPSLLPIPEQPGVTVLPALTHADVGLLRSLVG
```

Sequence Listing

*Spirochaeta thermophila* ATCC 49972 (Uniprot ID E0RT70) - SEQ ID NO: 5
MRKRRECAPPGIRAAIFDMDGTLVNSEDVYWDADCAFLDRYGIPHDDALREYMIGRGTKGFIEWMRTQKEIPRSDEEL
AREKMEVFLAHARGRVQVFPEMRRLLGLLEEAGMPCALASGSPRGIIEVLLEETGLAGFFRVVVSADEVARPKPAPDVF
LEEAGRLGVEPGGCVVFEDSEPGVRAGLDAGMVCVAIPTLVKDRYPEVFYQADVLFEGGMGEFSAERVWEWLGCGV
GVGR

*Sphaerobacter thermophilus* DSM 20745 (Uniprot ID D1C7G9) - SEQ ID NO: 6
MSQGVRGVVFDLDGLLVESEEYWEQARREFVSRYGGTWGDDAQQAVMGANTRQWSRYIREAFDIPLTEEEIAAAVI
ARMQELYHDHLPLLPGAIPAVRALADRYPLAVASSSPPVLIRFVLAEMGVAECFQSVTSSDEVAHGKPAPDVYHLACER
LGVAPEQAVAFEDSTAGIAAALAAGLRVIAVPNRSYPPDPDVLRRADLTLPSLEEFDPAVLEQW

4-glucan transferase

*Thermococcus litoralis* (Uniprot ID O32462) - SEQ ID NO: 12
MERINFIFGIHNHQPLGNFGWVFEEAYNRSYRPFMEILEEFPEMKVNVHFSGPLLEWIEENKPDYLDLLRSLIKRGQLEIV
VAGFYEPVLAAIPKEDRLVQIEMLKDYARKLGYDAKGVWLTERVWQPELVKSLREAGIEYVVVDDYHFMSAGLSKEELF
WPYYTEDGGEVITVFPIDEKLRYLIPFRPVKKTIEYLESLTSDDPSKVAVFHDDGEKFGVWPGTYEWVYEKGWLREFFDAI
TSNEKINLMTYSEYLSKFTPRGLVYLPIASYFEMSEWSLPAKQAKLFVEFVEQLKEEGKFEKYRVFVRGGIWKNFFFKYPE
SNFMHKRMLMVSKAVRDNPEARKYILKAQCNDAYWHGVFGGIYLPHLRRTVWENIIKAQRYLKPENKILDVDFDGRA
EIMVENDGFIATIKPHYGGSIFELSSKRKAVNYNDVLPRRWEHYHEVPEATKPEKESEEGIASIHELGKQIPEEIRRELAYD
WQLRAILQDHFIKPEETLDNYRLVKYHELGDFVNQPYEYEMIENGVKLWREGGVYAEEKIPARVEKKIELTEDGFIAKYR
VLLEKPYKALFGVEINLAVHSVMEKPEEFEAKEFEVNDPYGIGKVRIELDKAAKVWKFPIKTLSQSEAGWDFIQQGVSYT
MLFPIEKELEFTVRFREL

---

What is claimed is:

1. An improved process for the production of tagatose from a saccharide, the improved process comprising:
converting fructose-6-phosphate (F6P) to tagatose 6-phosphate (T6P) using a fructose 6-phosphate epimerase (F6PE) wherein the F6PE is selected from an amino acid sequence having at least 90% sequence identity to SEQ ID NO: 2 or SEQ ID NO: 7; and
converting T6P to tagatose using a tagatose 6-phosphate phosphatase (T6PP),
wherein the F6PE has a higher activity in the improved process compared to that of F6PE from *Dictyoglomus thermophilum* (Uniprot ID B5YBD7).

2. An improved process for the production of tagatose from a saccharide, the improved process comprising:
converting fructose-6-phosphate (F6P) to tagatose 6-phosphate (T6P) using a fructose 6-phosphate epimerase (F6PE); and
converting T6P to tagatose using a tagatose 6-phosphate phosphatase (T6PP), wherein the T6PP is selected from an amino acid sequence having at least 90% sequence identity to SEQ ID NO: 3, SEQ ID NO: 4, SEQ ID NO: 5, or SEQ ID NO: 6,
wherein the T6PP has a higher activity in the improved process compared to that of T6PP from *Archaeoglobus fulgidus* (Uniprot ID 029805).

3. The process of claim 2, further comprising a step of converting fructose-6-phosphate (F6P) to tagatose 6-phosphate (T6P) using a fructose 6-phosphate epimerase (F6PE) wherein the F6PE is selected from an amino acid sequence having at least 90% sequence identity to SEQ ID NO: 1, SEQ ID NO: 2, or SEQ ID NO: 7,
wherein the F6PE has a higher activity in the improved process compared to that of F6PE from *Dictyoglomus thermophilum* (Uniprot ID B5YBD7).

4. The process of claim 3, further comprising a step of converting glucose 6-phosphate (G6P) to the F6P, wherein the step is catalyzed by a phosphoglucose isomerase (PGI).

5. The process of claim 4, further comprising the step of converting glucose 1-phosphate (G1P) to the G6P, wherein the step is catalyzed by a phosphoglucomutase (PGM).

6. The process of claim 5, further comprising the step of converting the saccharide to the G1P, wherein the step is catalyzed by at least one enzyme, wherein the saccharide is selected from the group consisting of a starch or derivative thereof, cellulose or a derivative thereof and sucrose.

7. The process of claim 6, wherein the at least one enzyme is selected from the group consisting of alpha-glucan phosphorylase (αGP), maltose phosphorylase, sucrose phosphorylase, cellodextrin phosphorylase, cellobiose phosphorylase, and cellulose phosphorylase.

8. The process of claim 6, wherein the saccharide is a starch or a derivative thereof selected from the group consisting of amylose, amylopectin, soluble starch, amylodextrin, maltodextrin, maltose, maltotriose, and glucose.

9. The process of claim 8, further comprising the step of converting the starch to a starch derivative wherein the starch derivative is prepared by enzymatic hydrolysis or acid hydrolysis of the starch.

10. The process of claim 9, wherein a 4-glucan transferase (4GT) is added to the process.

11. The process of claim 9, wherein the starch derivative is prepared by enzymatic hydrolysis of the starch using an isoamylase, a pullulanase, an alpha-amylase, or a combination thereof.

12. The process of claim 3, further comprising a step of converting fructose to the F6P catalyzed by at least one enzyme.

13. The process of claim 4, further comprising a step of converting glucose to the G6P catalyzed by at least one enzyme.

14. The process of claim 3, wherein the process steps are conducted:
in a single reaction vessel;
at a temperature ranging from about 37° C. to about 85° C.;
at a pH ranging from about 5.0 to about 9.0;
for about 1 hour to about 48 hours; or
any combination of the above.

15. The process of claim 3, wherein the process steps are conducted:
without adenosine triphosphate (ATP) as a source of phosphate;
without nicotinamide adenosine dinucleotide;
at a phosphate concentration from about 0.1 mM to about 150 mM;
at a $Mg^{2+}$ concentration from about 0.1 mM to 50 mM;
wherein phosphate ions produced by T6PP dephosphorylation of T6P are used in the process step of converting the saccharide to G1P;
wherein at least one step of the process involves an energetically favorable chemical reaction; or
any combination of the above.

16. The process of claim 3, further comprising the step of separating and recovering the tagatose produced, wherein the separation and recovery is not via chromatography separation.

17. The process of claim 12, further comprising a step of converting sucrose to the fructose catalyzed by at least one enzyme.

18. The process of claim 13, further comprising a step of converting sucrose to the glucose catalyzed by at least one enzyme.

* * * * *